(12) United States Patent
Greenhut et al.

(10) Patent No.: US 9,241,640 B2
(45) Date of Patent: Jan. 26, 2016

(54) MEASUREMENT OF CARDIAC CYCLE LENGTH AND PRESSURE METRICS FROM PULMONARY ARTERIAL PRESSURE

(75) Inventors: Saul E. Greenhut, Aurora, CO (US); Robert T. Taepke, Coon Rapids, MN (US); David R. Bloem, Maple Grove, MN (US); Yong K. Cho, Maple Grove, MN (US); Donna M. Salmi, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 925 days.

(21) Appl. No.: 13/093,146

(22) Filed: Apr. 25, 2011

(65) Prior Publication Data
US 2012/0029364 A1 Feb. 2, 2012

Related U.S. Application Data

(60) Provisional application No. 61/368,437, filed on Jul. 28, 2010.

(51) Int. Cl.
*A61B 5/02* (2006.01)
*A61B 5/0215* (2006.01)
(Continued)

(52) U.S. Cl.
CPC .............. *A61B 5/0215* (2013.01); *A61B 5/024* (2013.01); *A61B 5/7239* (2013.01); *A61M 5/14276* (2013.01); *A61M 5/1723* (2013.01);
(Continued)

(58) Field of Classification Search
CPC .... A61B 5/7239; A61B 5/024; A61B 5/0215; A61M 5/14276; A61M 5/1723; A61N 1/36564; A61N 1/3962; A61N 1/03

USPC .......... 600/481, 483–486, 488, 500–503, 513
See application file for complete search history.

(56) References Cited

U.S. PATENT DOCUMENTS 4,566,456 A * 1/1986 Koning et al. ................... 607/23
5,368,040 A * 11/1994 Carney ........................... 600/513
(Continued)

FOREIGN PATENT DOCUMENTS

WO 2006081451 A1 8/2006
WO 2007068284 A1 6/2007
(Continued)

OTHER PUBLICATIONS

Jadvar H et al: "Computer analysis of right ventricular pressure for improved discrimination of ventricular tachyarrhythmias", Proceedings of the Computers in Cardiology Meeting. Chicago, Sep. 23, 1990, vol. Meeting 17, Sep. 23, 1990, pp. 35-38, XP010024737, ISBN: 978-0-8186-2225-0.*
(Continued)

*Primary Examiner* — Navin Natnithithadha
*Assistant Examiner* — Eric Messersmith
(74) *Attorney, Agent, or Firm* — Michael C. Soldner

(57) ABSTRACT

Various techniques for measuring cardiac cycle length and pressure metrics based on pulmonary artery pressures are described. One example method described includes identifying a point within a derivative signal of a cardiovascular pressure signal without reference to electrical activity of a heart, initiating a time window from the identified point in the derivative signal, identifying a point within the cardiovascular signal within the time window, and determining at least one of a systolic pressure or diastolic pressure based on the identified point.

25 Claims, 13 Drawing Sheets

(51) Int. Cl.
  *A61B 5/024* (2006.01)
  *A61M 5/142* (2006.01)
  *A61M 5/172* (2006.01)
  *A61N 1/365* (2006.01)
  *A61N 1/39* (2006.01)
  A61B 5/00 (2006.01)
  A61B 5/042 (2006.01)
  A61N 1/372 (2006.01)

(52) U.S. Cl.
  CPC .......... *A61N1/36564* (2013.01); *A61N 1/3962* (2013.01); *A61B 5/0031* (2013.01); *A61B 5/0422* (2013.01); *A61B 5/686* (2013.01); *A61B 5/6847* (2013.01); *A61B 5/6869* (2013.01); *A61B 5/6876* (2013.01); *A61M 2205/054* (2013.01); *A61M 2210/125* (2013.01); *A61N 1/37247* (2013.01)

(56) References Cited

U.S. PATENT DOCUMENTS

| | | | |
|---|---|---|---|
| 5,743,267 A * | 4/1998 | Nikolic et al. | 600/483 |
| 8,321,003 B2 | 11/2012 | Zhang et al. | |
| 2002/0019586 A1 | 2/2002 | Teller et al. | |
| 2005/0113647 A1 | 5/2005 | Lee et al. | |
| 2006/0167359 A1 | 7/2006 | Bennett et al. | |
| 2007/0060959 A1 | 3/2007 | Salo et al. | |
| 2007/0197921 A1* | 8/2007 | Cohen et al. | 600/485 |
| 2008/0195165 A1 | 8/2008 | Stahmann et al. | |
| 2008/0243016 A1 | 10/2008 | Liao et al. | |
| 2008/0300497 A1 | 12/2008 | Krause | |
| 2009/0048524 A1 | 2/2009 | Wildau et al. | |
| 2009/0299429 A1 | 12/2009 | Mayotte et al. | |
| 2010/0204592 A1 | 8/2010 | Hatib et al. | |
| 2011/0092827 A1* | 4/2011 | Hu et al. | 600/485 |
| 2012/0123232 A1 | 5/2012 | Najarian et al. | |

FOREIGN PATENT DOCUMENTS

| | | |
|---|---|---|
| WO | 2009025667 A1 | 2/2009 |
| WO | 2009134585 A1 | 11/2009 |

OTHER PUBLICATIONS

"#AS168—Analysis of Intraventricular Pressure Wave Data (LVP Analysis)" Biopac Document, 1996, Retrieved from the Internet on Aug. 19, 2013. <URL: http://www.biopac.com/Manuals/app_pdf/app168_mp.pdf>.*

Reynolds et al., "Measurement of pulmonary artery diastolic pressure from the right ventricle," Journal of the American College of Cardiology, vol. 25, No. 5, Apr. 1, 1995, pp. 1176-1182.

Jadvar et al., "Computer analysis of right ventricular pressure for improved discrimination of ventricular tachyarrhythmias," Proceedings of the Computers in Cardiology Meeting, Chicago, IL, meeting 17, Sep. 23, 1990, pp. 35-38.

Ohlsson et al., "Continuous ambulatory haemodynamic monitoring with an implantable system. The feasibility of a new technique," European Heart Journal, vol. 19, No. 1, Jan. 1998, pp. 174-184.

Yoon et al., "Automated analysis of intracardiac blood pressure waveforms for implantable defibrillators," Computers in Cardiology, vol. 25, Sep. 13, 1998, pp. 269-272.

International Search Report and Written Opinion of international application No. PCT/US2011/045571, dated Nov. 17, 2011, 18 pp.

International Search Report and Written Opinion of international application No. PCT/US2011/045575, dated Nov. 21, 2011, 16 pp.

Beckers et al, "ACTS: Automated Calculation of Tachograms and Systograms," Progress in Biomedical Research, Apr. 1999, pp. 160-165.

Office Action from U.S. Appl. No. 13/096,166, dated Aug. 29, 2013, 9 pp.

Response to Office Action dated Aug. 29, 2013, from U.S. Appl. No. 13/093,166, filed Dec. 6, 2013, 8 pp.

Response to Office Action dated Apr. 16, 2014, from U.S. Appl. No. 13/093,166, filed on Aug. 18, 2014, 13 pp.

Office Action from U.S. Appl. No. 13/093,166, dated Apr. 16, 2014, 11 pp.

* cited by examiner

MEASUREMENT OF CARDIAC CYCLE LENGTH AND PRESSURE METRICS FROM PULMONARY ARTERIAL PRESSURE

RELATED APPLICATION

The present disclosure claims priority and other benefits from U.S. Provisional Patent Application Ser. No. 61/368,437, filed Jul. 28, 2010, entitled "MEASUREMENT OF CARDIAC CYCLE LENGTH AND PRESSURE METRICS FROM PULMONARY ARTERIAL PRESSURE", incorporated herein by reference in its entirety.

TECHNICAL FIELD

The disclosure relates to medical devices and, more particularly, to implantable medical devices that monitor cardiac pressure.

BACKGROUND

A variety of implantable medical devices for delivering a therapy and/or monitoring a physiological condition have been clinically implanted or proposed for clinical implantation in patients. Implantable medical devices may deliver electrical stimulation or drug therapy to, and/or monitor conditions associated with, the heart, muscle, nerve, brain, stomach or other organs or tissue, as examples. Implantable medical devices may include or be coupled to one or more physiological sensors, which may be used in conjunction with the device to provide signals related to various physiological conditions from which a patient state or the need for a therapy can be assessed.

Some implantable medical devices may employ one or more elongated electrical leads carrying stimulation electrodes, sense electrodes, and/or other sensors. Implantable medical leads may be configured to allow electrodes or other sensors to be positioned at desired locations for delivery of stimulation or sensing. For example, electrodes or sensors may be carried at a distal portion of a lead. A proximal portion of the lead may be coupled to an implantable medical device housing, which may contain circuitry such as stimulation generation and/or sensing circuitry. Other implantable medical devices may employ one or more catheters through which the devices deliver a therapeutic fluid to a target site within a patient. Examples of such implantable medical devices include heart monitors, pacemakers, implantable cardioverter defibrillators (ICDs), myostimulators, neurostimulators, therapeutic fluid delivery devices, insulin pumps, and glucose monitors.

Pressure sensors may be employed in conjunction with implantable medical devices as physiological sensors configured to detect changes in blood pressure. Example pressure sensors that may be useful for measuring blood pressure may employ capacitive, piezoelectric, piezoresistive, electromagnetic, optical, resonant-frequency, or thermal methods of pressure transduction.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
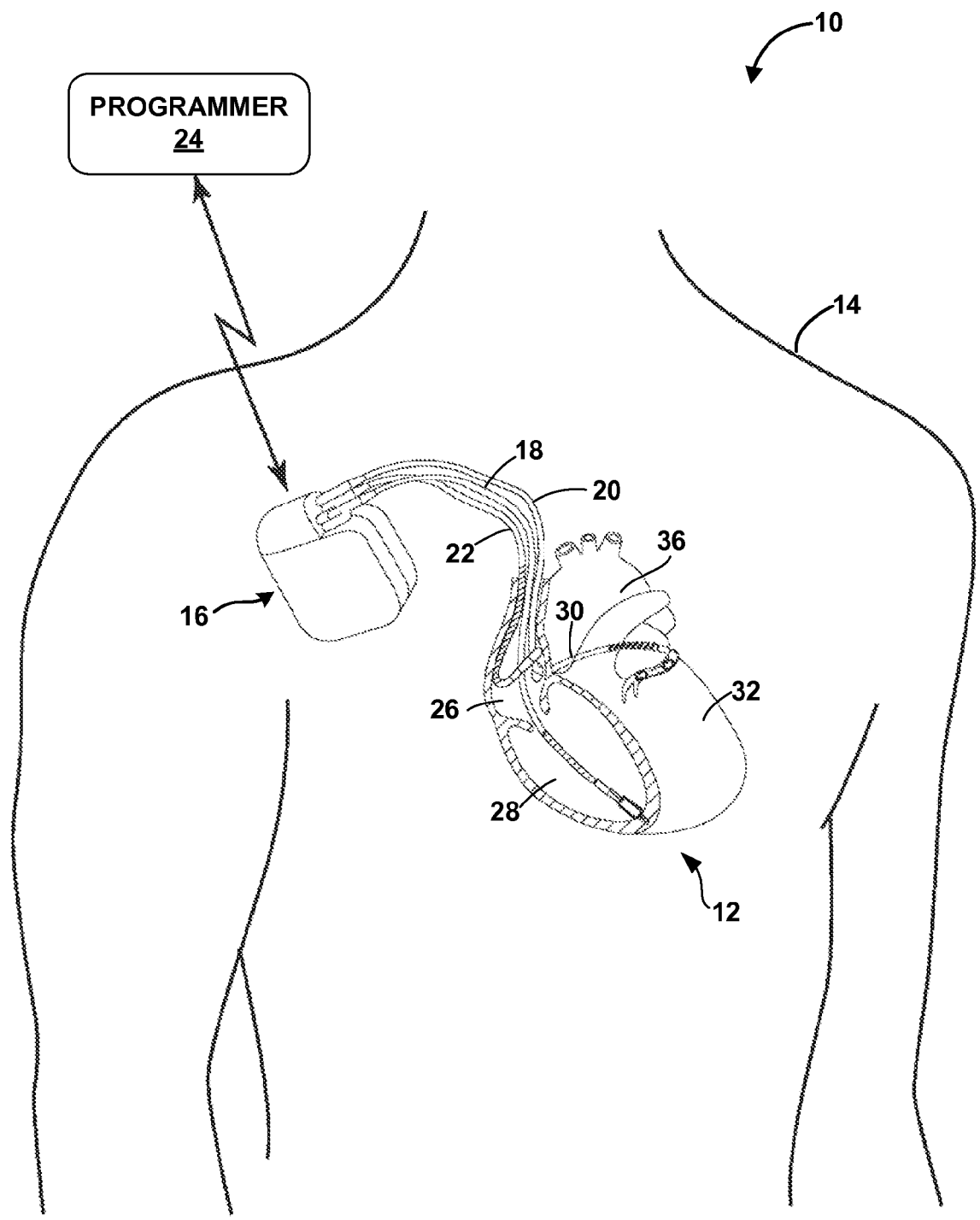
FIG. 1 is a conceptual diagram illustrating an example system that may be used to provide therapy to and/or monitor a heart of a patient.

In general, this disclosure describes techniques for cardiovascular monitoring. The cardiovascular monitoring techniques may include determining a cardiac cycle length and/or cardiovascular pressure metrics such as systolic pressure and diastolic pressure from a pressure signal detected by a pressure sensor implanted within the pulmonary artery of a patient. In some cases, a derivative of the pressure signal may be used to determine the cardiac cycle length and/or the cardiac pressure metrics. Additionally, second or higher order derivatives may be taken in order to identify other morphological fiducial points on the pressure waveform that contribute to measurements with clinical diagnostic value. Averaging and cross correlation or mathematical transform techniques may also be used for this purpose. Using the techniques of this disclosure, an implantable medical device may deliver drug therapy or therapeutic electrical stimulation, or acquire diagnostic information, based on the determined cardiac cycle length and/or various pressure metrics.

In one example, the disclosure is directed to a method comprising identifying, by a medical device, a point within a derivative signal of a cardiovascular pressure signal without reference to electrical activity of a heart, initiating, by the medical device, a time window from the identified point in the derivative signal, identifying, with the medical device, a point within the cardiovascular signal within the time window, and determining, with the medical device, at least one of a systolic pressure or diastolic pressure based on the identified point.

In another example, the disclosure is directed to a system comprising at least one pressure sensor, and at least one pressure analysis module configured to identify a point within a derivative signal of a cardiovascular pressure signal without reference to electrical activity of a heart, initiate a time window from the identified point in the derivative signal, identify a point within the cardiovascular signal within the time window, and determine at least one of a systolic pressure or diastolic pressure based on the identified point.

In another example, the disclosure is directed to a computer-readable storage medium comprising instructions that, when executed, cause a pressure analysis module to identify a point within a derivative signal of a cardiovascular pressure signal without reference to electrical activity of a heart, initiate a time window from the identified point in the derivative signal, identify a point within the cardiovascular signal within the time window, and determine at least one of a systolic pressure or diastolic pressure based on the identified point.

In another example, the disclosure is directed to a method comprising identifying, by a medical device, a plurality of fiducial points within a derivative signal of a cardiovascular pressure signal, and identifying, by the medical device, a length of time between consecutive ones of the fiducial points as a cardiac cycle length, wherein identifying the plurality of fiducial points comprises comparing the derivative signal to a threshold, identifying a point within the derivative signal that satisfies the threshold, identifying the fiducial point within the derivative signal subsequent to the point within the derivative signal that satisfies the threshold, and initiating a blanking period that begins at the fiducial point, and wherein comparing the derivative signal to the threshold comprises not comparing the derivative signal to the threshold for identification of a subsequent one of the fiducial points during the blanking period.

A system comprising at least one pressure sensor, and at least one pressure analysis module configured to identify a plurality of fiducial points within a derivative signal of a cardiovascular pressure signal, and identify a length of time between consecutive ones of the fiducial points as a cardiac cycle length, wherein the at least one pressure analysis module configured to identify the plurality of fiducial points is further configured to compare the derivative signal to a threshold, identify a point within the derivative signal that satisfies the threshold, identify the fiducial point within the derivative signal subsequent to the point within the derivative signal that satisfies the threshold, and initiate a blanking period that begins at the fiducial point, and wherein at least one pressure analysis module configured to compare the derivative signal to the threshold is configured to not compare the derivative signal to the threshold for identification of a subsequent one of the fiducial points during the blanking period.

A computer-readable storage medium comprising instructions that, when executed, cause a pressure analysis module to identify a plurality of fiducial points within a derivative signal of a cardiovascular pressure signal, and identify a length of time between consecutive ones of the fiducial points as a cardiac cycle length, wherein the instructions that, when executed, cause a pressure analysis module to identify the plurality of fiducial points comprise instructions that, when executed, cause the pressure analysis module to compare the derivative signal to a threshold, identify a point within the derivative signal that satisfies the threshold, identify the fiducial point within the derivative signal subsequent to the point within the derivative signal that satisfies the threshold, and initiate a blanking period that begins at the fiducial point, and wherein the instructions that, when executed, cause a pressure analysis module to compare the derivative signal to the threshold comprise instructions that, when executed, cause the pressure analysis module to not compare the derivative signal to the threshold for identification of a subsequent one of the fiducial points during the blanking period.

The details of one or more aspects of the disclosure are set forth in the accompanying drawings and the description below. Other features, objects, and advantages will be apparent from the description and drawings, and from the claims.

This disclosure describes various techniques for measuring cardiac cycle length and pressure metrics based on pulmonary artery pressures. Cardiac cycle length is often measured by sensing ventricular electrical depolarizations from an electrocardiogram (ECG) or intracardiac electrogram (EGM). However, because it may be desirable to limit the amount of hardware implanted within a patient and computing requirements, electrical measurements may not be available. Using the techniques of this disclosure, cardiac cycle length and pressure metrics such as systolic pressure and diastolic pressure may be derived from the pulmonary arterial pressure (PAP) from one or more pressure sensors in the pulmonary artery (PA), and without using a cardiac electrical signal. In this manner, cardiac cycle lengths, for example, may be determined without adding electrodes to a patient. It is understood that the techniques described in this disclosure may also be applied to measuring cardiac cycle length and pressure metrics based on ventricular pressure with wired or wireless sensors located within the right ventricle (RV).

FIG. 1 is a schematic view of an implantable medical device. FIG. 1 is a conceptual diagram illustrating an example system 10 that may be used to monitor and/or provide therapy to heart 12 of patient 14. Patient 14 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. In accordance with certain techniques of this disclosure, IMD 16 may receive pressure information from a pressure sensor (not shown in FIG. 1) located within a pulmonary artery of patient 14 and, in some examples, provide electrical signals to heart 12 based on the received pressure information, as will be described in greater detail below. The pressure sensor may be coupled to IMD 16 via a lead, or wirelessly.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, and 22, or a power source of IMD 16. The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
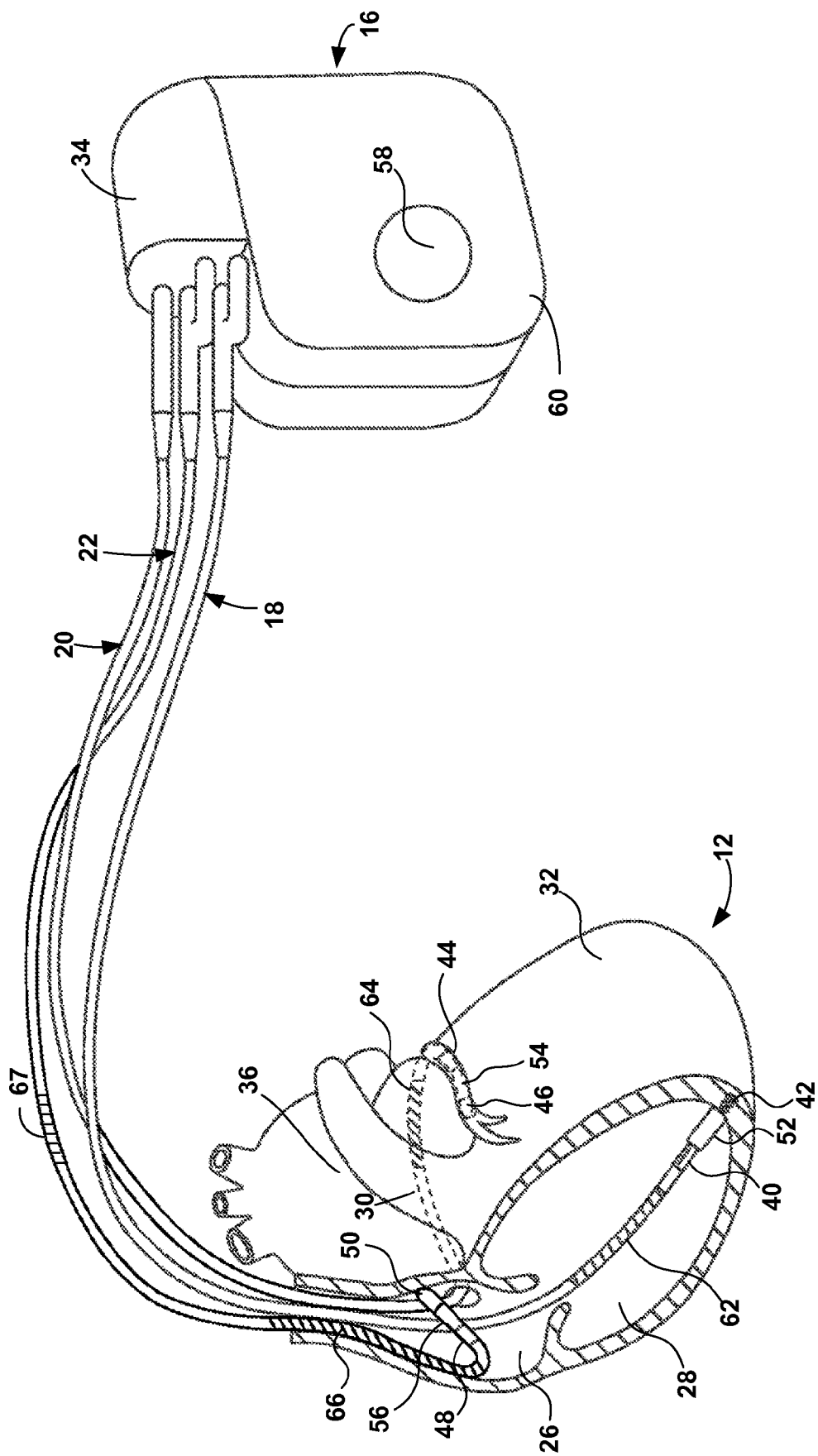
FIG. 2 is a conceptual diagram illustrating the example implantable medical device (IMD) and the leads of the system shown in FIG. 1 in greater detail.

FIG. 2 is a conceptual diagram illustrating IMD 16 and leads 18, 20, and 22 of therapy system 10 in greater detail. Leads 18, 20, 22 may be electrically coupled to a signal generator and a sensing module of IMD 16 via connector block 34.

Each of the leads 18, 20, 22 includes an elongated insulative lead body carrying one or more conductors. Bipolar electrodes 40 and 42 are located adjacent to a distal end of lead 18. In addition, bipolar electrodes 44 and 46 are located adjacent to a distal end of lead 20 and bipolar electrodes 48 and 50 are located adjacent to a distal end of lead 22. Electrodes 40, 44 and 48 may take the form of ring electrodes, and electrodes 42, 46 and 50 may take the form of extendable helix tip electrodes mounted retractably within insulative electrode heads 52, 54 and 56, respectively.

Leads 18, 20, 22 also include elongated intracardiac electrodes 62, 64 and 66 respectively, which may take the form of a coil. In addition, one of leads 18, 20, 22, e.g., lead 22 as seen in FIG. 2, may include a superior vena cava (SVC) coil 67 for delivery of electrical stimulation, e.g., transvenous defibrillation. For example, lead 22 may be inserted through the superior vena cava and SVC coil 67 may be placed, for example, at the right atrial/SVC junction (low SVC) or in the left subclavian vein (high SVC). Each of the electrodes 40, 42, 44, 46, 48, 50, 62, 64, 66 and 67 may be electrically coupled to a respective one of the conductors within the lead body of its associated lead 18, 20, 22, and thereby individually coupled to the signal generator and sensing module of IMD 16. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60.

IMD 16 may sense electrical signals attendant to the depolarization and repolarization of heart 12 via electrodes 40, 42, 44, 46, 48, 50, 58, 62, 64, 66 and 67. The electrical signals are conducted to IMD 16 via the respective leads 18, 20, 22, or in the case of housing electrode 58, a conductor coupled to the housing electrode. IMD 16 may sense such electrical signals via any bipolar combination of electrodes 40, 42, 44, 46, 48, 50, 58, 62, 64, 66 and 67. Furthermore, any of the electrodes 40, 42, 44, 46, 48, 50, 58, 62, 64, 66 and 67 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. For example, electrodes 40, 42, and/or 58 may be used to deliver RV pacing to heart 12. Additionally or alternatively, electrodes 44, 46, and/or 58 may be used to deliver LV pacing to heart 12, and electrodes 48, 50 and/or 58 may be used to deliver RA pacing to heart 12.

Furthermore, IMD 16 may deliver defibrillation pulses to heart 12 via any combination of elongated electrodes 62, 64, 66 and 67, and housing electrode 58. Electrodes 58, 62, 64, 66 may also be used to deliver cardioversion pulses to heart 12. Electrodes 62, 64, 66 and 67 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIGS. 1 and 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. Other examples of therapy systems may include a single lead that extends from IMD 16 into right atrium 26 or right ventricle 28, or two leads that extend into a respective one of the right ventricle 28 and right atrium 26 (not shown). The example of FIGS. 1 and 2 includes a single electrode per chamber of heart 12 engaged with the wall of heart 12, e.g., free wall, for that chamber. Other examples may include multiple electrodes per chamber, at a variety of different locations on the wall of heart. The multiple electrodes may be carried by one lead or multiple leads per chamber.

In accordance with certain aspects of this disclosure, one or more pressure sensors located in a pulmonary artery of a patient may communicate with IMD 16 via wireless communication, or may be coupled to IMD 16 via one or more leads. For example, the pressure sensor(s) may communicate pressure information, e.g., data, that represents a pressure signal that is a function of a pressure in heart 12, to IMD 16. In response, IMD 16 and, in particular, a processor of IMD 16, may determine a cardiac cycle length or various pressure metrics, as described in more detail below.

For conciseness, the disclosure generally refers to IMD 16 as performing any computations, but the disclosure is not so limited. In other examples, the pressure sensor(s) may communicate the pressure information to programmer 24. In response, programmer 24 may determine a cardiac cycle length or various pressure metrics, as described in more detail below. In other examples, the pressure sensor(s) may communicate the pressure information to another device, e.g., a computing device, server, network, or the like, for storage and/or analysis.

Furthermore, in other examples, the pressure sensor may itself analyze pressure information to determine, for example, a cardiac cycle length or various pressure metrics using the various techniques described herein. In such examples, the pressure sensor may store the cycle length and other metrics, and may communicate, e.g., wirelessly, the cycle length and other metrics to IMD 16, programmer 24, or another computing device.

Figure 3:
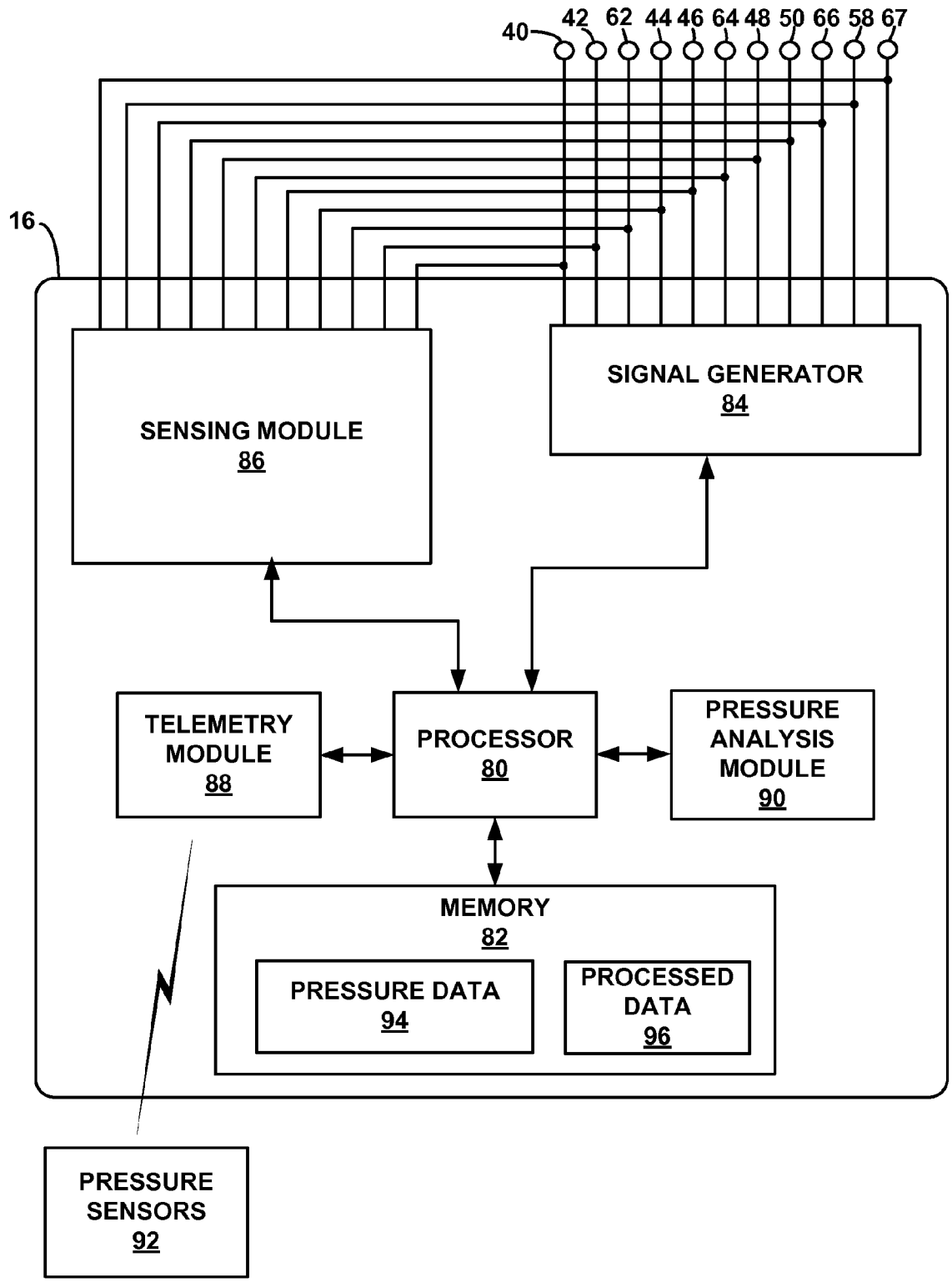
FIG. 3 is a functional block diagram illustrating an exemplary configuration of the IMD of FIG. 1.

FIG. 3 is a functional block diagram illustrating an exemplary configuration of IMD 16 that may be used to implement certain techniques of this disclosure. In the illustrated example, IMD 16 includes a processor 80, memory 82, signal generator 84, sensing module 86, telemetry module 88, and pressure analysis module 90. As seen in FIG. 3, one or more pressure sensors 92 may be in communication with IMD 16 via telemetry module 88. Pressure analysis module 90 analyzes the pressure data received from pressure sensor(s) 92. Pressure analysis module 90 may be implemented as software, firmware, hardware or any combination thereof. In some example implementations, pressure analysis module 90 may be a software process implemented in or executed by processor 80. Memory 82 is one example of a non-transitory, computer-readable storage medium that includes computer-readable instructions that, when executed by processor 80, cause IMD 16 and processor 80 to perform various functions attributed to IMD 16 and processor 80 in this disclosure. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

As indicated above, the techniques for measuring cardiac cycle length and pressure metrics based on pulmonary artery pressures described in this disclosure need not be used in conjunction with IMD 16. However, in some example implementations, one or more pressure sensors 92 may communicate pressure information, e.g., data, that represents a pressure signal of a pressure in heart 12 to IMD 16. In response, IMD 16 and, in particular, pressure analysis module 90, may perform some or all of the calculations described below in order to determine a cardiac cycle length and/or various pressure metrics.

In some example implementations, implantable medical devices may deliver drug therapy based on the determined cardiac cycle length and/or various pressure metrics, as described in more detail below with respect to FIG. 13. In other example implementations, processor 80 of IMD 16 may control signal generator 84 to deliver stimulation therapy to heart 12 based on the determined cardiac cycle length or various pressure metrics. For example, upon receiving pressure information representing a pressure signal from a pressure sensor, pressure analysis module 90 may determine that the systolic pressure in the pulmonary artery is below a predetermined threshold value. In response, processor 80 may, for example, control signal generator 84 to deliver pacing pulses to heart 12 to increase the amount of blood flow. Processor 80 may also adjust pacing settings in response to the determination.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof.

In some examples, processor 80 controls signal generator 84 to deliver stimulation therapy to heart 12 according to a selected one or more of therapy programs, which may be stored in memory 82. For example, processor 80 may control signal generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, 66, and 67 e.g., via conductors of the respective lead 18, 20, 22, or, in the case of housing electrode 58, via an electrical conductor disposed within housing 60 of IMD 16. In some examples, signal generator 84 is configured to generate and deliver electrical stimulation therapy to heart 12. For example, signal generator 84 may deliver defibrillation shocks as therapy to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module, and processor 80 may use the switch module to select which of the available electrodes are used to deliver such stimulation. The switch module may include a switch array, switch matrix, multiplexer, or any other type of switching device suitable to selectively couple stimulation energy to selected electrodes.

In some examples, sensing module 86 monitors signals from at least one of electrodes 40, 42, 44, 46, 48, 50, 58, 62, 64, 66 or 67 in order to monitor electrical activity of heart 12. Sensing module 86 may also include a switch module. In some examples, processor 80 may select the electrodes that function as sense electrodes via the switch module within sensing module 86.

Sensing module 86 may include one or more detection channels (not shown), each of which may comprise an amplifier. The detection channels may be used to sense the cardiac signals. Some detection channels may detect cardiac events, such as R- or P-waves, and provide indications of the occurrences of such events to processor 80. One or more other detection channels may provide the signals to an analog-to-digital converter, for processing or analysis by processor 80. In some examples, processor 80 may store the digitized versions of signals from one or more selected detection channels in memory 82 as EGM signals. In response to the signals from processor 80, the switch module within sensing module 86 may couple selected electrodes to selected detection channels, e.g., for detecting events or acquiring an EGM in a particular chamber of heart 12.

For some patients, it may be desirable to limit the amount of hardware implanted. As such, at least some of the electrical measurements that may be sensed by sensing module 86 may not be available to IMD 16. Using various techniques of this disclosure, cardiac cycle length and/or pressure metrics such as peak-systolic pressure and end-diastolic pressure may be derived from the pulmonary arterial pressure (PAP) from one or more pressure sensors 92 in the pulmonary artery (PA). In this manner, cardiac cycle lengths, for example, may be determined without adding electrodes to a patient.

Processor 80 may maintain interval counters, such as A-A, V-V, A-V, RV-LV, A-RV, or A-LV interval counters. Processor 80 may reset such counters upon sensing of R-waves and P-waves with detection channels of sensing module 86. Processor 80 may also control signal generator 84 to deliver pacing pulses when the interval counters reach a predetermined value without being reset, and then reset the escape interval counters upon the delivery of the pacing pulses by signal generator 84. In this manner, processor 80 may control the basic timing of cardiac pacing functions, including anti-tachyarrhythmia pacing, based on pressure data.

The value of the count present in the interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect a suspected tachyarrhythmia event, such as ventricular fibrillation or ventricular tachycardia. In some examples, processor 80 may determine that tachyarrhythmia has occurred by identification of shortened R-R (or P-P) interval lengths. An interval length below a threshold may need to be detected for a certain number of consecutive cycles, or for a certain percentage of cycles within a running window, as examples. In some examples, processor 80 may additionally or alternatively employ digital signal analysis techniques to characterize one or more digitized signals from the detection channels of sensing module 86 to detect and classify tachyarrhythmias.

As illustrated in FIG. 3, in addition to program instructions, memory 82 may store pressure data 94 received from pressure sensor 92 via telemetry module 88. Processor 80 may store pressure information received from pressure sensor 92 as pressure data 94. Pressure data 94 may include raw, unprocessed pressure information that represents a pressure signal within a pulmonary artery of a patient. In other examples, processor 80 may store pressure information processed by pressure analysis module 90 in memory 82 as processed data 96. Processed data 96 may represent the values determined based on pressure data 94, such as cycle lengths, averages, trends over time. In particular, processed data 96 may include cycle length data, systolic pressure data, and diastolic pressure data as processed and/or determined by pressure analysis module 90. In addition, in some example implementations, processor 80 may control pressure sensor 92 to measure a pressure within a pulmonary artery of a patient. For example, based on predetermined timing data stored in memory 82, or timing data transmitted via a programmer, e.g., programmer 24, processor 80 may transmit, via telemetry module 88, instructions to pressure sensor 92 to take one or more pressure measurements.

Figure 4:
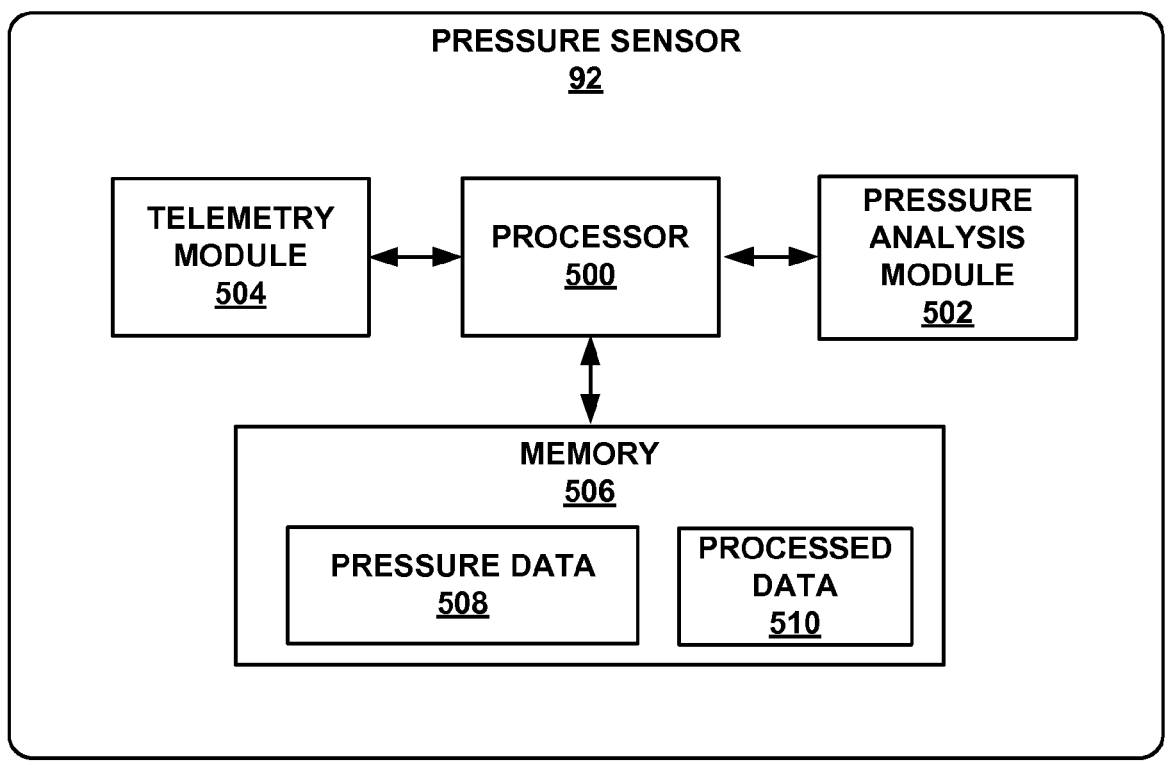
FIG. 4 is a functional block diagram illustrating an exemplary configuration of a pressure sensor that may be used to implement certain techniques of this disclosure.

FIG. 4 is a functional block diagram illustrating an exemplary configuration of a pressure sensor that may be used to implement certain techniques of this disclosure. In the illustrated example, pressure sensor 92 includes a processor 500, pressure analysis module 502, telemetry module 504, and memory 506. Processor 500 and telemetry module 504 may be similar to processor 80 and telemetry module 88 of FIG. 3. Processor 500 may store pressure information as pressure data 508 in memory 506. Pressure data 508 may include raw, unprocessed pressure information that represents a pressure signal within a pulmonary artery of a patient. In some examples, telemetry module 504 may transmit pressure data 508 to IMD 16 for processing. In other examples, telemetry module 504 may transmit pressure data 508 to programmer 24, or to another external device, e.g., for further analysis.

In some examples, pressure analysis module 502 may process pressure information sensed by pressure sensor 92 and store the processed information in memory 506 as processor data 510. Pressure analysis module 502 may be implemented as software, firmware, hardware or any combination thereof. In some example implementations, pressure analysis module 502 may be a software process implemented in or executed by processor 500. Processed data 510 may represent the values determined based on pressure data 508, such as cycle lengths, averages, trends over time. In particular, processed data 510 may include cycle length data, systolic pressure data, and diastolic pressure data as processed and/or determined by pressure analysis module 502. Then, telemetry module 504 may transmit processed data 510 to IMD 16, programmer 24, or another external device, e.g., for further analysis.

Figure 5:
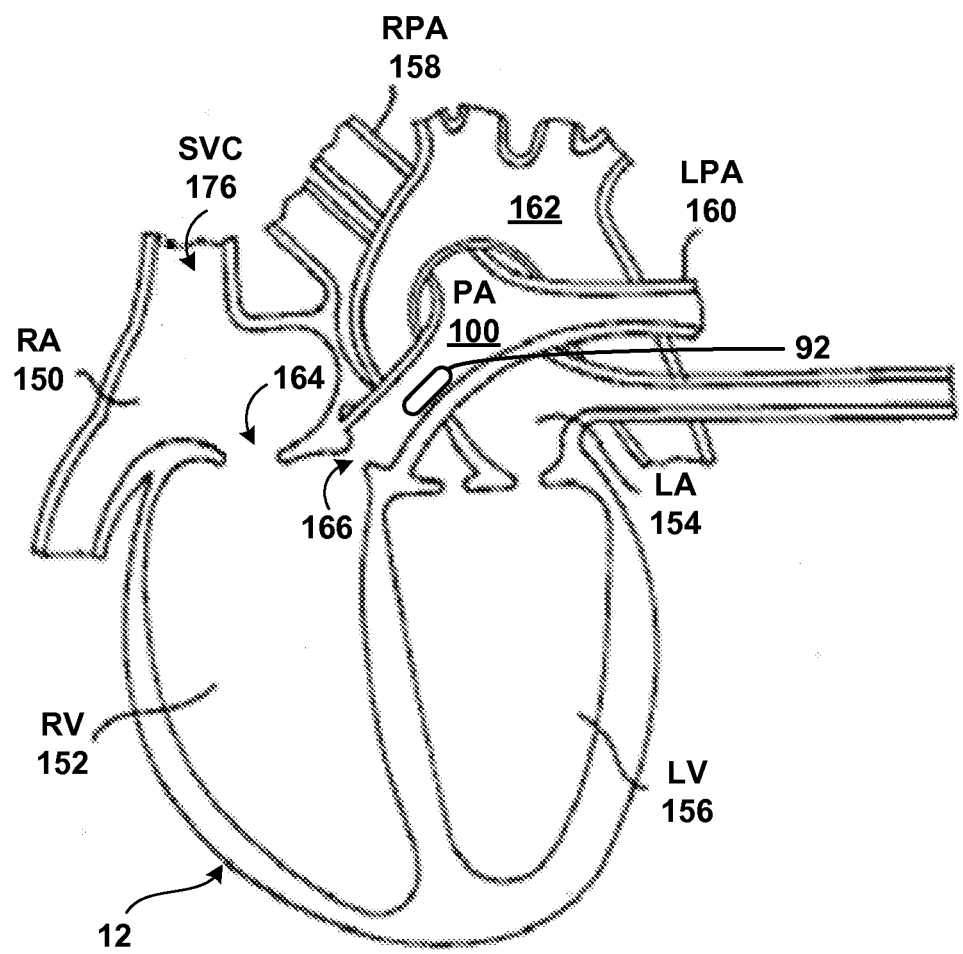
FIG. 5 is a diagram of a human heart, including a pressure sensor.

FIG. 5 is a diagram of a human heart, including a leadless pressure sensor. Heart 12 of FIG. 5 depicts pulmonary artery 100, right atrium 150, right ventricle 152, left atrium 154, left ventricle 156, right pulmonary artery 158, left pulmonary artery 160, aorta 162, atrioventricular valve 164, pulmonary valve 166, aortic valve 168, and superior vena cava 176. Pressure sensor 92 may, as shown in FIG. 5, be placed inside pulmonary artery 100 of heart 12. In some example implementations, sensor 92 may be placed within main pulmonary artery 100, the right pulmonary artery 158 or any of its branches, and/or within left pulmonary artery 160 or any of its branches, or within the right ventricle. In other example implementations, multiple pressure sensors 92 may be placed at various locations within pulmonary artery 100, right pulmonary artery 158 or any of its branches, and/or left pulmonary artery 160 or any of its branches.

As shown in FIG. 5, pressure sensor 92 may be a leadless assembly, e.g., need not be coupled to an IMD or other device via a lead, and need not otherwise be coupled to any leads. Although not depicted, pressure sensor 92 may include wireless communication capabilities such as low frequency or radiofrequency (RF) telemetry, as well other wireless communication techniques that allow sensor 92 to communicate with IMD 16, programmer 24, or another device. Pressure sensor 92 may be affixed to the wall of the pulmonary artery or the wall of the right ventricle using any number of well-known techniques. For example, pressure sensor 92 may include fixation elements, e.g., helical tines, hooked tines, barbs, or the like, that allow sensor 92 to be secured to pulmonary artery 100. In other examples, pressure sensor 92 may be attached to a stent having any variety of conformations, for example, and the stent/sensor combination may be implanted within pulmonary artery 100.

Pressure sensor 92 may be implanted within pulmonary artery 100, for example, using a delivery catheter. For example, a physician may deliver pressure sensor(s) 92 via a delivery catheter, transvenously through either the internal jugular or femoral veins. The delivery catheter then extends through superior vena cava 176, right atrioventricular valve 164, right ventricle 152, and pulmonary valve 166 into pulmonary artery 100. In other examples, pressure sensor 92 may be implanted after a physician has opened the patient's chest by cutting through the sternum.

Pressure sensor 92 generates pressure information representing a pressure signal as a function of the fluid pressure in pulmonary artery 100, for example. IMD 16, programmer 24, and/or another device, e.g., external monitoring equipment, may receive, monitor, and analyze the pressure information, as will be described in more detail below, in order to determine a cardiac cycle length and/or other pressure metrics. In other examples, pressure sensor 92 may itself analyze the pressure information in order to determine a cardiac cycle length and/or other pressure metrics according to the techniques described herein.

Figure 6:
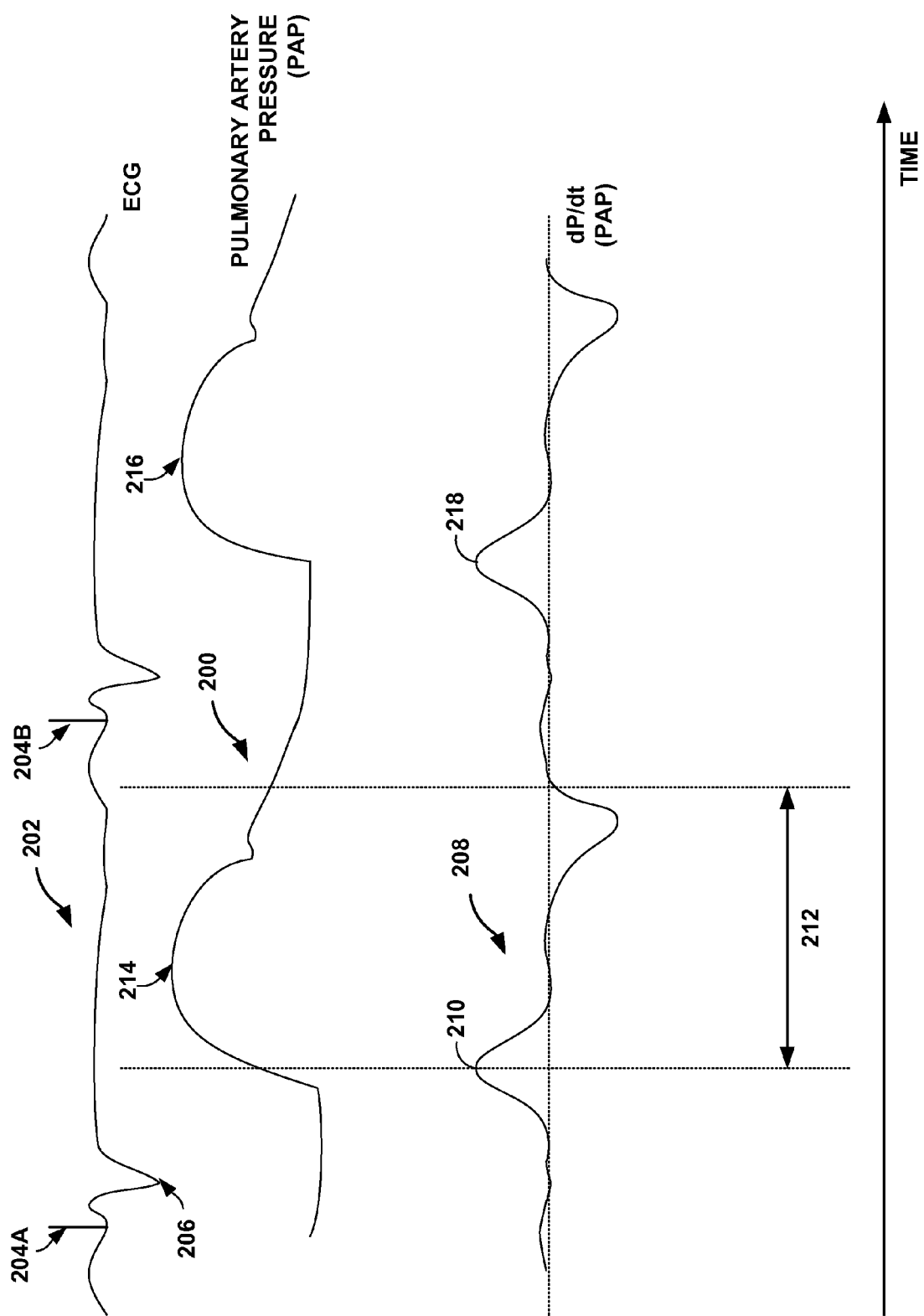
FIG. 6 is a timing diagram showing a signal indicative of pulmonary arterial pressure, and the first derivative of the pulmonary arterial pressure signal, which may be used to determine a systolic pressure, in accordance with certain techniques of this disclosure.

FIG. 6 is a timing diagram showing a signal indicative of pulmonary arterial pressure, and the first derivative of the pulmonary arterial pressure signal, which may be used to determine a systolic pressure, in accordance with certain techniques of this disclosure. Pulmonary artery pressure signal 200 from pressure sensor 92 in pulmonary artery 100 is shown in reference to electrocardiogram (ECG) signal 202. ECG signal 202 shows pacing spikes 204A and 204B. ECG signal 202 may be sensed by electrodes, as described above in detail with respect to FIG. 2. R-wave 206 in ECG signal 202 of FIG. 6 represents ventricular depolarization of heart 12. ECG signal 202 is shown for reference purposes only. The techniques of this disclosure need not use or rely upon ECG signal 202 in order to determine cardiac cycle lengths.

Using certain techniques of this disclosure, various pressures measured during systole, e.g., peak-systolic pressure, may be determined from pulmonary artery pressure signal 200 and derivatives, e.g., dP/dt signal 208, derived therefrom. Briefly, in order to determine peak-systolic pressure, for example, a point of maximum value, e.g., peak, in the first derivative of a pressure signal is identified, the pressure signal being a function of a pressure in heart 12. After identifying the point in the first derivative of the pressure signal, a time window is initiated that begins at the point of maximum value and that extends forward in time. Peak-systolic pressure is determined by identifying a maximum value of pulmonary artery pressure signal 200 within the time window. Using the techniques of this disclosure, a peak-systolic pressure may be determined without reference to electrical activity of the heart.

This technique for determining peak-systolic pressure is described with reference to FIG. 6 as follows. The slope in pulmonary artery pressure signal 200 is shown graphically as dP/dt signal 208, i.e., the first order derivative of pressure with respect to time. A maximum value in the first derivative of the pressure signal, i.e., peak dP/dt, is identified, as shown at 210 in dP/dt signal 208. The peak dP/dt may be determined via a threshold crossing algorithm, e.g., the threshold crossing algorithm used to sense PAP waveforms. A window may be initiated once dP/dt exceeds a threshold value and either $d^2P/dt^2$ is greater than zero or a number "n" samples, e.g., 1-3, are below the threshold value prior to becoming suprathreshold. The window may be approximately 100 milliseconds to about 200 milliseconds in length. A maximum value in the first derivative of the pressure signal, i.e., peak dP/dt, is identified within this window.

A time window that extends forward in time, e.g., time window 212, is initiated at the peak in the first derivative of the pressure signal, e.g., point 210 of dP/dt signal 208. The time window may be predetermined, or its duration may be modulated adaptively, based on one or more other physiologic variables, e.g., heart rate. Peak-systolic pressure is determined by identifying a maximum value of pulmonary artery pressure signal 200 within time window 212, as indicated at 214. In this manner, peak-systolic pressure may be determined without the use of invasive electrodes or other hardware. Delivery of a therapeutic substance or therapeutic electrical stimulation, e.g., via IMD 16, may be controlled based on the identified maximum value of the pressure signal, i.e., the peak-systolic pressure. In some example implementations, pressure information may be determined and stored, without adjusting therapy based on the information.

Figure 7:
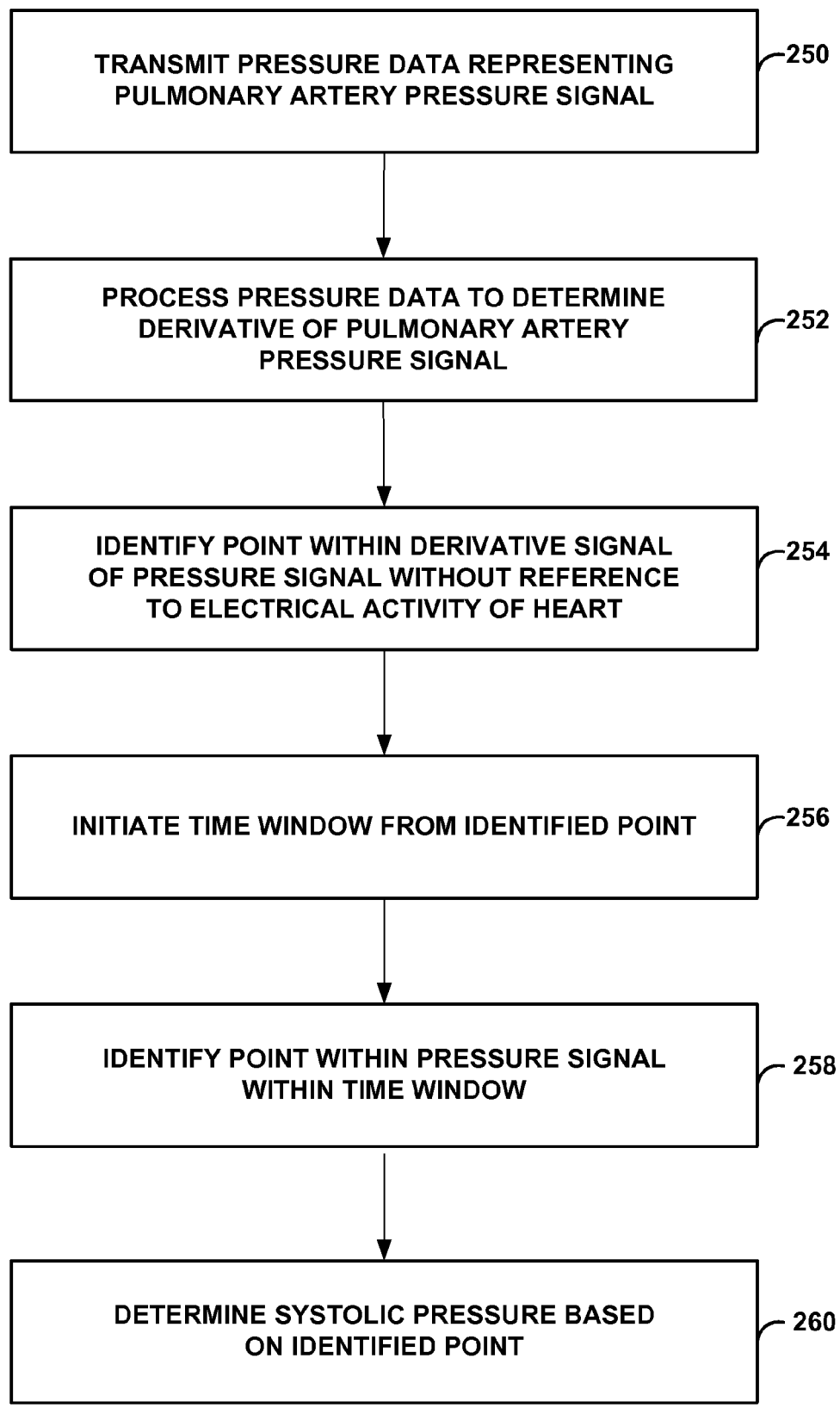
FIG. 7 is a flow diagram illustrating an exemplary method for determining systolic pressure, in accordance with various techniques of this disclosure.

FIG. 7 is a flow diagram illustrating an exemplary method for determining systolic pressure, in accordance with various techniques of this disclosure. As indicated above, pressure analysis module 90 of IMD 16 (FIG. 3) or pressure analysis module 502 of pressure sensor 92 (FIG. 4) may be used to perform some or all of the calculations described above in order to calculate systolic pressure. For example, pressure sensor 92 (FIG. 3) may transmit pressure information, or data, representing pulmonary artery pressure signal 200 to a processor, e.g., processor 80 (FIG. 3), via telemetry module 88 (FIG. 3) (250). In response, processor 80 stores the received pressure information in memory 82 (FIG. 3) as pressure data 94 and then pressure analysis module 90 (FIG. 3) processes pressure data 94 (FIG. 3) by applying a high pass filter, e.g., a derivative filter, to pressure data 94 to determine a derivative, e.g., first, second, or other higher derivative, of pulmonary artery signal 200 (252). In other words, pressure analysis module 90 generates a plurality of points of slope in the pressure signal. Filtering the pressure information may reduce or eliminate noise caused by respiration. By applying a first order derivative filter to pulmonary artery signal 200, pressure analysis module 90 determines the slope of pulmonary artery signal 200 e.g., dP/dt signal 208, and helps identify sections of the signal with the greatest rate of change. It should be noted that, in some examples, pressure analysis module 90 processes the pressure information received from pressure sensor 92 without first storing the information in memory 82.

After applying a first order derivative filter to pulmonary artery signal 200 to determine a slope of pulmonary artery signal 200, pressure analysis module 90 identifies a point within a derivative signal of a cardiovascular pressure signal without reference to electrical activity of a heart (254). In particular, pressure analysis module 90 identifies a maximum value of the first derivative signal. Pressure analysis module 90 then initiates a time window, e.g., time window 212 of FIG. 6, which extends forward in time from the maximum value (256). The length of the time window may be stored as a parameter within memory 82 of IMD 16, for example. The time window may have a fixed length, e.g., about 50 milliseconds (ms) to about 500 ms, that may be user configurable or otherwise preprogrammed.

In other examples, the time window may have a variable length which may adapt to physiological conditions. For example, the time window may decrease in length if the heart rate increases or increase in length if the heart rate decreases. To provide an adaptive time window, pressure analysis module 90 may, for example, determine the mean, median, mode, or the like (referred to collectively as an "average") of several cardiac cycle length measurements, which may be determined as described below, compare the determined average cycle length to one or more predetermined threshold values, or a function, lookup table, or the like, and then adjust the time window accordingly to account for any increase or decrease in heart rate.

The cardiac cycle length may be determined from the pulmonary artery pressure signal as the length of time between any two corresponding points, e.g., maximum values, in pulmonary artery pressure signal 200. For example, the time between points 214 and 216 in pulmonary artery pressure signal 200 represents a cardiac cycle, and thus a cardiac cycle length. Similarly, cardiac cycle length may be determined from derivative signal 208 as the length of time between any two corresponding points, e.g., peaks, of the derivative signal. For example, the time between points 210 and 218 in first derivative signal 208 represents a cardiac cycle length. Regardless of whether time window 212 of FIG. 6 is fixed or adaptive, pressure analysis module 90 identifies a point within the cardiovascular pressure signal within the time window (258). Then, pressure analysis module 90 determines a systolic pressure based on the identified point (260). In particular, pressure analysis module 90 determines, within the time window, a maximum value of pulmonary artery pressure signal 200, which corresponds to the peak-systolic pressure. If there is a group of adjacent points of the pressure waveform within time window 212 that all have the maximal value (i.e., the PA pressure peak has a small flattened area), then an algorithm may be used to choose one of those identically-valued points. Examples include choosing the first point in the group, choosing the last point, or choosing a middle point. If the points that all had the maximal value were not adjacent, a similar rule may be used to choose the point to be deemed the correct peak-systolic pressure and its time of occurrence.

Although the determination of peak-systolic pressure was described above with respect to pressure analysis module 90, as mentioned above, pressure analysis module 502 of pressure sensor 92, a pressure analysis module of programmer 24, or a pressure analysis module of another device, may be used to determine peak-systolic pressure using the techniques of this disclosure. In some examples, a pressure analysis module may be implemented in one or more devices identified herein, such as one or more processors of the devices such as pressure sensor 92, IMD 16, and programmer 24 to determine peak-systolic pressure using the techniques of this disclosure.

In addition to determining peak-systolic pressure within a pulmonary artery, e.g., pulmonary artery 100, various techniques of this disclosure may be used to determine a diastolic pressure, e.g., an end-diastolic pressure, within the pulmonary artery, as described below with respect to FIG. 8.

Figure 8:
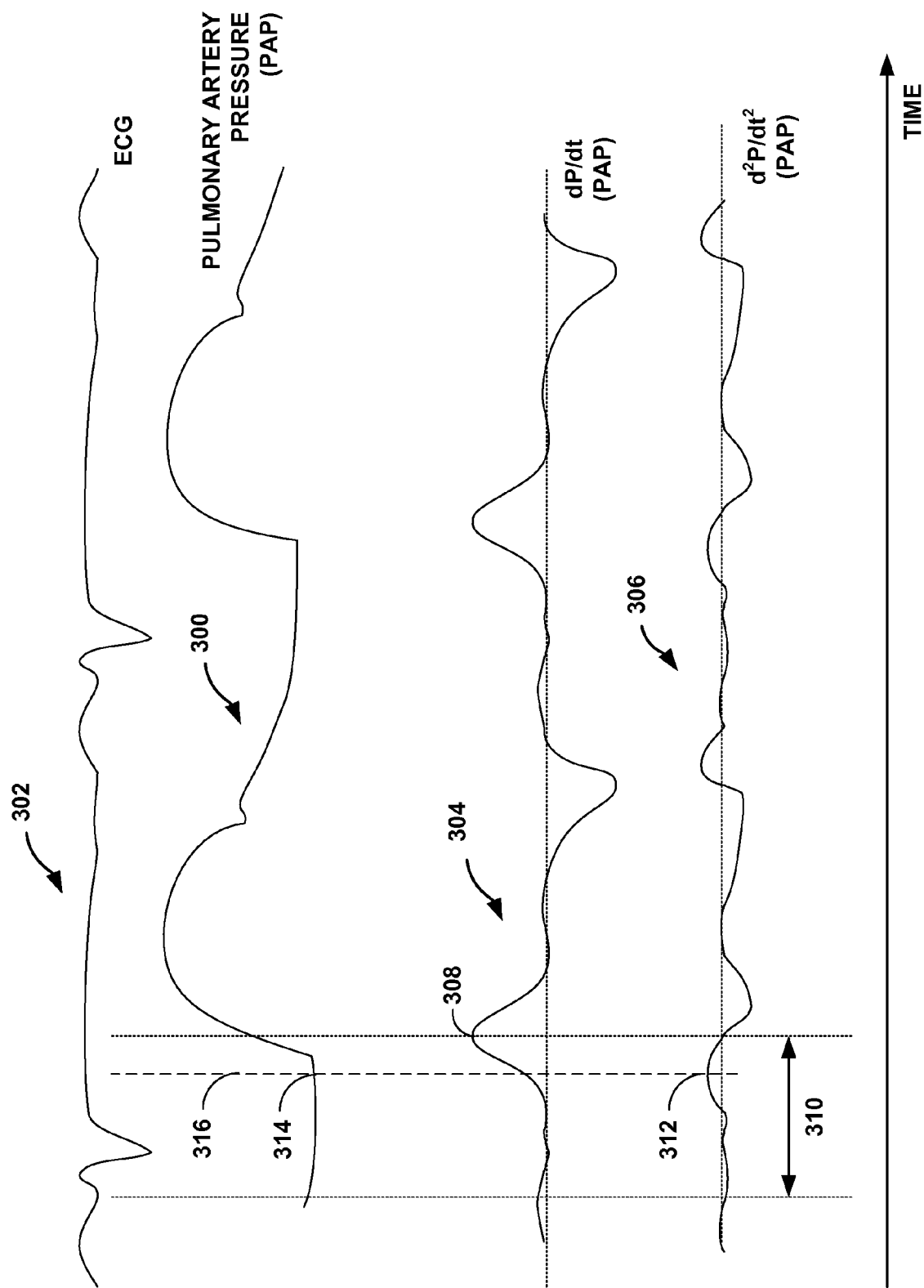
FIG. 8 is a timing diagram showing a signal indicative of pulmonary arterial pressure, and the first and second derivatives of the pulmonary arterial pressure signal, which may be used to determine a diastolic pressure, in accordance with certain techniques of this disclosure.

FIG. 8 is a timing diagram showing a signal indicative of pulmonary arterial pressure, and the first and second derivatives of the pulmonary arterial pressure signal, which may be used to determine a diastolic pressure, in accordance with certain techniques of this disclosure.

Similar to FIG. 6, FIG. 8 depicts pulmonary artery pressure signal 300 from pressure sensor 92 (FIG. 3) in pulmonary artery 100 in reference to electrocardiogram (ECG) signal 302. ECG signal 302 is shown for reference purposes only. The techniques of this disclosure do not use or rely upon ECG signal 302. Using certain techniques of this disclosure, various pressures measured during diastole, e.g., end-diastolic pressure, may be determined from pulmonary artery pressure signal 300 and derivatives, e.g., dP/dt signal 304 and $d^2P/dt^2$ signal 306, derived therefrom. In order to determine end-diastolic pressure, for example, a point of maximum value, e.g., peak, in the first derivative of a pressure signal is identified, the pressure signal being a function of a pressure in heart 12. After identifying the point in the first derivative of the pressure signal, a time window is initiated that begins at the point of maximum value and that extends backward in time. Then, a point of maximum second derivative within the time window is identified. An end-diastolic pressure is determined by identifying the point on the pulmonary artery pressure signal 300 within the time window that corresponds in time to the point of maximum second derivative. If there is a group of adjacent points of the second derivative that all have the maximal value (i.e., the second derivative peak has a small flattened area), then an algorithm may be used to choose one of those identically-valued points. Examples include choosing the first point in the group, choosing the last point, or choosing a middle point. If the points that all had the maximal value were not adjacent, a similar rule may be used to choose the point to be deemed the correct end-diastolic pressure and its time of occurrence. Using certain techniques of this disclosure, an end-diastolic pressure may be determined without reference to electrical activity of the heart.

This technique for determining end-diastolic pressure is described with reference to FIG. 8 as follows. The slope in pulmonary artery pressure signal 300 is shown graphically as dP/dt signal 304, i.e., the first order derivative of pulmonary artery pressure with respect to time. A point of maximum value in the first derivative of the pulmonary artery pressure, i.e., peak dP/dt, is shown at 308 in dP/dt signal 304. The peak dP/dt may be determined via a threshold crossing algorithm, e.g., the threshold crossing algorithm used to sense PAP waveforms. A window may be initiated once dP/dt exceeds a threshold value and either $d^2P/dt^2$ is greater than zero or a number "n" samples, e.g., 1-3, are below the threshold value prior to becoming suprathreshold. The window may be about 100 milliseconds to about 200 milliseconds in length. The maximum value in the first derivative of the pulmonary artery pressure, i.e., peak dP/dt, is identified within this window.

A time window, e.g., time window 310, which extends backward in time is initiated at the point of maximum value in the first derivative of the pressure signal, e.g., point 308 of dP/dt signal 304. Then, a point of maximum second derivative (an inflection point) within time window 310 is identified, as shown at 312 in $d^2P/dt^2$ signal 306. An end-diastolic pressure is then determined by identifying the value of pulmonary artery pressure signal 300 within time window 310 that corresponds in time to the point of maximum second derivative, as shown at 314 by the intersection of dashed line 316 and pulmonary artery pressure signal 300. In this manner, an end-diastolic pressure may be determined without the use of invasive electrodes or other hardware. Delivery of a therapeutic substance or therapeutic electrical stimulation, e.g., via IMD 16, may be controlled based on the identified maximum value of the second derivative of the pressure signal, i.e., the end-diastolic pressure. In some example implementations, pressure information may be determined and stored, without adjusting therapy based on the information.

Figure 9:
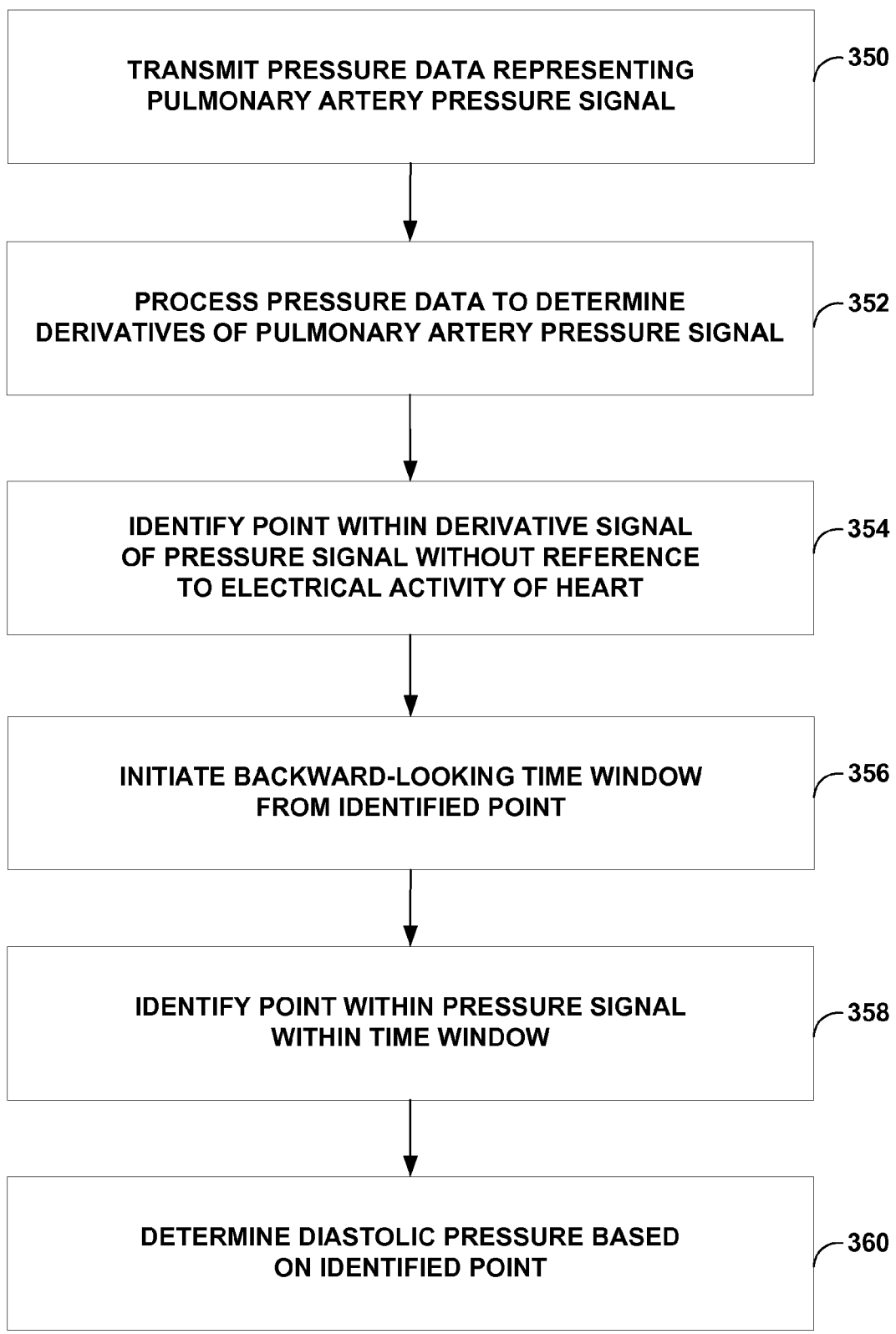
FIG. 9 is a flow diagram illustrating an exemplary method for determining a diastolic pressure, in accordance with various techniques of this disclosure.

FIG. 9 is a flow diagram illustrating an exemplary method for determining an end-diastolic pressure, in accordance with various techniques of this disclosure. As mentioned above, a pressure analysis module, e.g., pressure analysis module 90 of IMD 16 (FIG. 3), may be used to perform some or all of the calculations described above in order to calculate an end-diastolic pressure. For example, pressure sensor 92 (FIG. 3) may transmit pressure information representing pulmonary artery pressure signal 200 to processor 80 (FIG. 3) via telemetry module 88 (FIG. 3) (350). In response, processor 80 stores the received pressure information in memory 82 (FIG. 3) as pressure data 94 (FIG. 3) and then pressure analysis module 90 (FIG. 3) processes pressure data 94 by applying high pass filters, e.g., derivative filters, to pressure data 94 to determine first and second order derivatives of pulmonary artery signal 300 (352). By applying a first order derivative filter to pulmonary artery signal 300, pressure analysis module 90 determines the slope of pulmonary artery signal 300, e.g., dP/dt signal 304. By applying a second order derivative filter to pulmonary artery signal 300, pressure analysis module 90 determines the second derivative of pulmonary artery signal 300, e.g., $d^2P/dt^2$ signal 306. It should be noted that, in some examples, pressure analysis module 90 processes the pressure information received from pressure sensor 92 without first storing the information in memory 82.

After applying derivative filters to pulmonary artery signal 300, pressure analysis module 90 identifies a point within a derivative signal of a cardiovascular pressure signal without reference to electrical activity of a heart (354). In particular, pressure analysis module 90 identifies a point of maximum value from the determined slope, e.g., point 308. Pressure analysis module 90 then initiates a time window, e.g., time window 310 of FIG. 8, from the identified point which extends backward in time from the point of maximum value (356). The length of the time window may be stored as a parameter within memory 82 of IMD 16, for example. The time window may have a fixed length that may be user configurable or otherwise preprogrammed. In one example of a time window having a fixed length, the time window may be set such that the end-diastolic pressure is identified within 200 ms, for example, prior to the identified maximum dP/dt value. In some examples, the time window may have variable length which may adapt to physiological conditions, such as cardiac cycle length, as described above with respect to determination of systolic pressure and FIG. 6.

Within the time window, e.g., time window 310 of FIG. 8, pressure analysis module 90 identifies a point of maximum second derivative within time window 310, e.g., point 312 in $d^2P/dt^2$ signal 306. Pressure analysis module 90 then identifies a point within the cardiovascular signal within the time window (358). Then pressure analysis module 90 determines an end-diastolic pressure based on the identified point (360). In particular, pressure analysis module 90 determines an end-diastolic pressure by identifying the value of the pulmonary artery pressure signal 300 within time window 310 that corresponds in time to the point of maximum second derivative, e.g., point 314. In this manner, an end-diastolic pressure may be determined without the use of invasive electrodes or other hardware.

Although the determination of end-diastolic pressure was described above with respect to pressure analysis module 90, as mentioned above, pressure analysis module 502 of pressure sensor 92, a pressure analysis module of programmer 24, or a pressure analysis module of another device, may be used to determine end-diastolic pressure using the techniques of this disclosure. In some examples, a pressure analysis module may be implemented in one or more devices identified herein, such as one or more processors of the devices such as pressure sensor 92, IMD 16, and programmer 24 to determine end-diastolic pressure using the techniques of this disclosure.

In addition to pressure metrics such as end-diastolic and systolic pressures, various techniques of this disclosure may be used to determine a cardiac cycle length, as described in detail below with respect to FIG. 10. A cardiac cycle is the complete cycle of events in the heart, and a cardiac cycle length is the amount of time between a first event of a first heart beat and a corresponding second event of a second heart beat that immediately follows the first heart beat.

Figure 10:
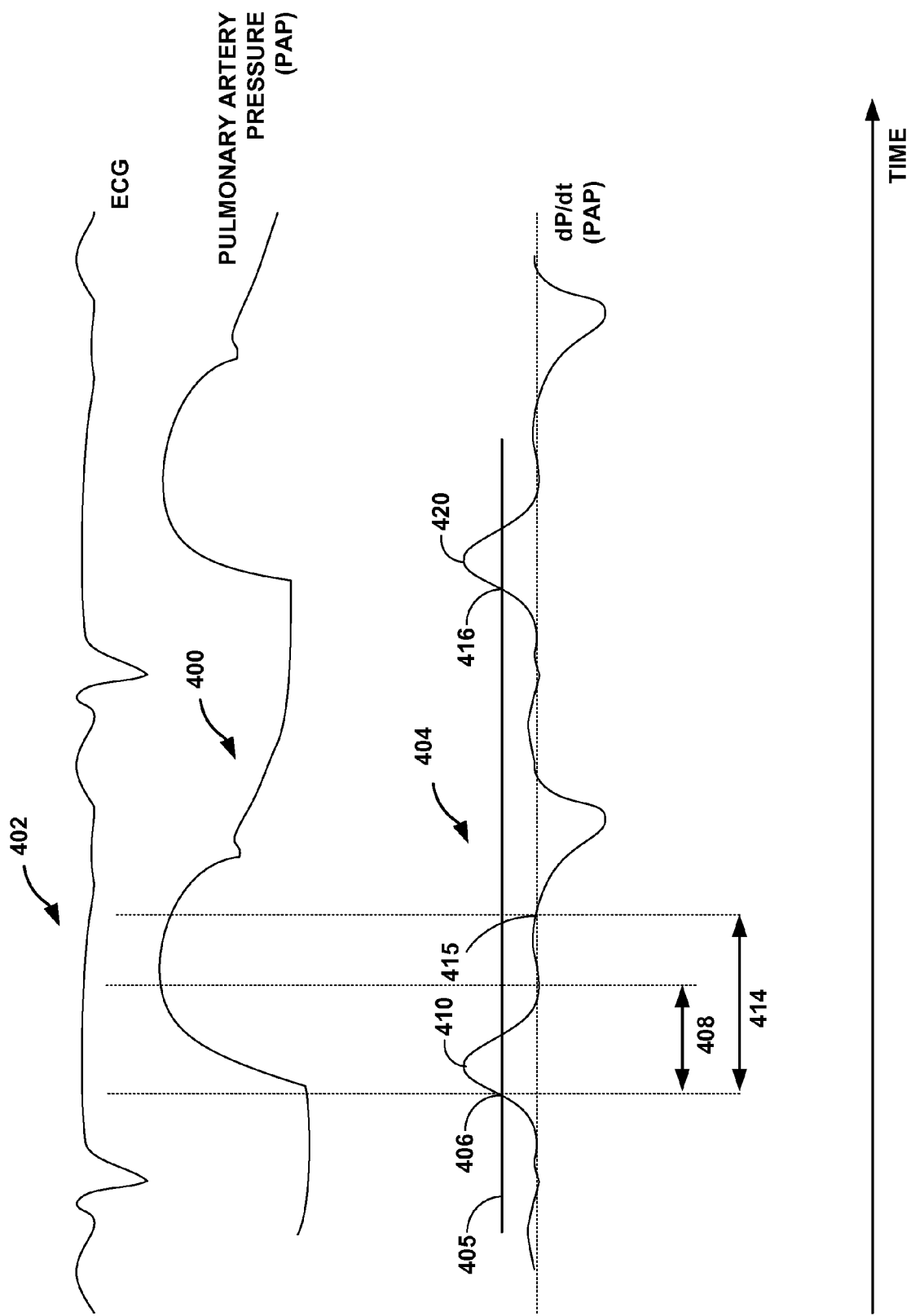
FIG. 10 is a timing diagram showing a signal indicative of pulmonary arterial pressure, and the first derivative of the pulmonary arterial pressure signal, which may be used to determine a cardiac cycle length, in accordance with certain techniques of this disclosure.

FIG. 10 is a timing diagram showing a signal indicative of pulmonary arterial pressure, and the first derivative of the pulmonary arterial pressure signal, which may be used to determine a cardiac cycle length, in accordance with certain techniques of this disclosure. FIG. 10 depicts pulmonary artery pressure signal 400 from pressure sensor 92 in pulmonary artery 100 in reference to electrocardiogram (ECG) signal 402. ECG signal 402 is shown for reference purposes only. The techniques of this disclosure do not use or rely upon ECG signal 402.

An exemplary technique for determining a length of a cardiac cycle is described with reference to FIG. 10 as follows. The slope in pulmonary artery pressure signal 400 is shown graphically as dP/dt signal 404, i.e., the first order derivative of pulmonary artery pressure with respect to time. First order derivative signal 404 comprises a plurality of points of slope. A first one of the plurality of points of slope of signal 404 that is greater than a threshold value, indicated by line 405, is identified, as shown at 406. Useful thresholds in humans span the approximate range of about 40 mmHg/s to about 600 mmHg/s. The thresholds are specified to the algorithm in mmHg/W, where "W" is the window duration over which the derivative is estimated. For example, if the derivative was estimated over 4 samples at a sampling frequency of 128 Hz, then W, the window length, would be 4/128 Hz=0.0313 seconds. Then, if the optimal threshold with this derivative estimator was found to be 16 mmHg/W, the corresponding derivative threshold in mmHg/s would be 16/0.0313=512 mmHg/s. Higher values may be useful in non-human subjects. This identified point may also be referred to as a "sense," i.e., a suprathreshold value of the first order derivative of the pulmonary artery pressure signal. In some example implementations, the threshold value may be a fixed value. In other example implementations, the threshold value may be adaptive and adapt to changing physiological conditions. For example, the threshold may vary with the value of the last dP/dt maximum. The threshold could also decrease with time from some function of the previous dP/dt maximum.

In addition to dP/dt being suprathreshold, i.e., satisfying the threshold, there may be additional conditions before identifying the "sense." One example condition is that $d^2P/dt^2$ be greater than zero when dP/dt becomes suprathreshold. This condition may help ensure that the signal is rising when the sense is identified. Another example condition is to make sure that a number "n" samples of dP/dt, e.g., 1-3 samples, are below the threshold prior to becoming suprathreshold. This may help ensure that there was a "−" to "+" threshold cross. These conditions may be useful when the signal first exits the blanking period.

After a sense, i.e., after a point of slope of signal 404 that is greater than a threshold value is identified, e.g., point 406 in FIG. 10, a first time window is initiated that extends forward in time, e.g., time window 408. During first time window 408, a first point of maximum value of dP/dt signal 404 is identified, depicted in FIG. 10 at 410. Time window 408 may have a length of about 200 ms to about 400 ms, for example.

First time window 408 is searched until the first point of maximum value of dP/dt signal 404 is identified, e.g., maximum value 410. Then, a second one of the plurality of points of slope in the pressure signal within the time window 408 is identified, e.g., first point of maximum value of dP/dt 410. This second one of the plurality of points of slope serves as a first reference point for determining the length of the cardiac cycle. As described below, a corresponding second reference point is identified and the cardiac cycle length is the time between the first and second reference points. For example, a corresponding second reference point may be a second point of maximum value of dP/dt, shown at 420. In such an example, the cardiac cycle length is the time between point 410 and point 420. In other examples, the first reference point may be first sense 406, the second reference point may be second sense 416, and the cardiac cycle length is the time between point 406 and 416. In another example, the cardiac cycle length may be determined instead between two peak-systolic pressures, or between two end-diastolic pressures. It should be noted that any pre-defined point derived from pressure or dP/dt may be used as a cardiac cycle delimiter.

A second time window, e.g., time window 414, that extends forward in time to second time 415 may be initiated at the first sense. The second time window 414 is greater than the first time window 408 and therefore extends beyond the first time window 408, i.e., later in time than the first time window 408. The second time window 414 represents a blanking period, e.g., an idle period, during which the determination of a sense, i.e., identification of a point of slope signal 404 being greater than the threshold value 405, is no longer made in order to prevent extraneous measurements caused by respiration, cardiac variations, and the like from being sensed by pressure sensor 92. The effective blanking period is actually the time from the first sense, e.g., point 406, to second time 415, i.e., second time window 414. Second time 415, i.e., the end of the effective blanking period, is determined by finding the time at which the peak-systolic pressure occurs and adding a blanking period, e.g., about 100 milliseconds to about 300 milliseconds. This blanking technique may prevent double senses in the event that pressure increases because of respiration, e.g., at the beginning of expiration, or because of normal cardiac-caused waveform variations, e.g., the dicrotic notch. By determining the end of the blanking period from the time of peak-systolic pressure, i.e., terminating the blanking period based on a time since peak-systolic pressure, this technique also results in a rate adaptive blanking period. Because the time from the sense to the maximum pressure decreases as heart rate increases, the effective blanking period also decreases as rate increases. Using various techniques of this disclosure may help to prevent missed senses at higher heart rates, while providing adequate blanking at lower heart rates. The minimum detected cycle length is equal to the effective blanking period, i.e., second time window 414 and the maximum heart rate equals 60,000 divided by the minimum detected cycle length.

The effective blanking period described above, i.e., second time window 414, may be rate adaptive and adapt to physiological conditions in additional ways to that described above. For example, the blanking period may be timed from the sense and made rate adaptive with respect to measured heart rate, e.g., decrease in duration if the heart rate increases or increase in duration if the heart rate decreases. To provide an adaptive blanking period, a processor may, for example, determine the mean, median, mode, or the like (referred to collectively as an "average") of several cycle lengths of the pulmonary artery pressure signal, of a first derivative signal, or of a higher order derivative signal, compare the determined average cycle length to a predetermined threshold value, and then adjust the blanking window accordingly to account for any increase or decrease in heart rate. In other examples, the blanking period may be fixed. For example, a fixed blanking period may be initiated at the first sense, e.g., point 406.

After the blanking period represented by second time window 414 has expired, a third one of the plurality of points of slope of signal 404 that is greater than the threshold value, indicated by line 405, is identified, as shown at 416. In other words, a third one of the plurality of points of slope of signal 404 that is greater than the threshold value is identified outside the second time window, e.g., time window 414. This identified point may also be referred to as a second "sense," i.e., a suprathreshold value of the first order derivative of the pulmonary artery pressure signal. In addition to dP/dt being suprathreshold, there may be additional conditions before identifying the "sense," as described above.

After identifying the third one of the plurality of points of slope of signal 404, i.e., the second sense, shown at 416, a fourth one of the plurality of points of slope in the pressure signal that corresponds in dP/dt signal 404, i.e., the slope in the pressure signal, to the previously identified second one of the plurality of points of slope in the pressure signal within the first time window. This fourth one of the plurality of points of slope serves as a second reference point for determining the length of the cardiac cycle. For example, if first point of maximum value of dP/dt 410 was selected as a first reference point, then second point of maximum value of dP/dt 420 should be selected as the corresponding second reference point. Or, if first sense 406 was selected as the first reference point, then second sense 416 should be selected as the corresponding second reference point. Although described above with respect to a first maximum value of dP/dt and a second maximum value of dP/dt and a first sense and a second sense, a cardiac cycle length may be measured also be measured between a first end-diastolic pressure and a second end-diastolic pressure and a first peak-systolic pressure and a second peak-systolic pressure.

Finally, a difference in time is determined between the identified fourth one of the plurality of points of slope in the pressure signal, e.g., the second reference point shown at 420 in FIG. 10, and the identified second one of the plurality of points of slope in the pressure signal within the first time window, e.g., the first reference point shown at 410 in FIG. 10. This difference in time represents the length of the cardiac cycle. Delivery of a therapeutic substance or therapeutic electrical stimulation, e.g., via IMD 16, may be controlled based on the determined difference in time, i.e., the cardiac cycle length. In some example implementations, pressure information may be determined and stored, without adjusting therapy based on the information.

Figure 11:
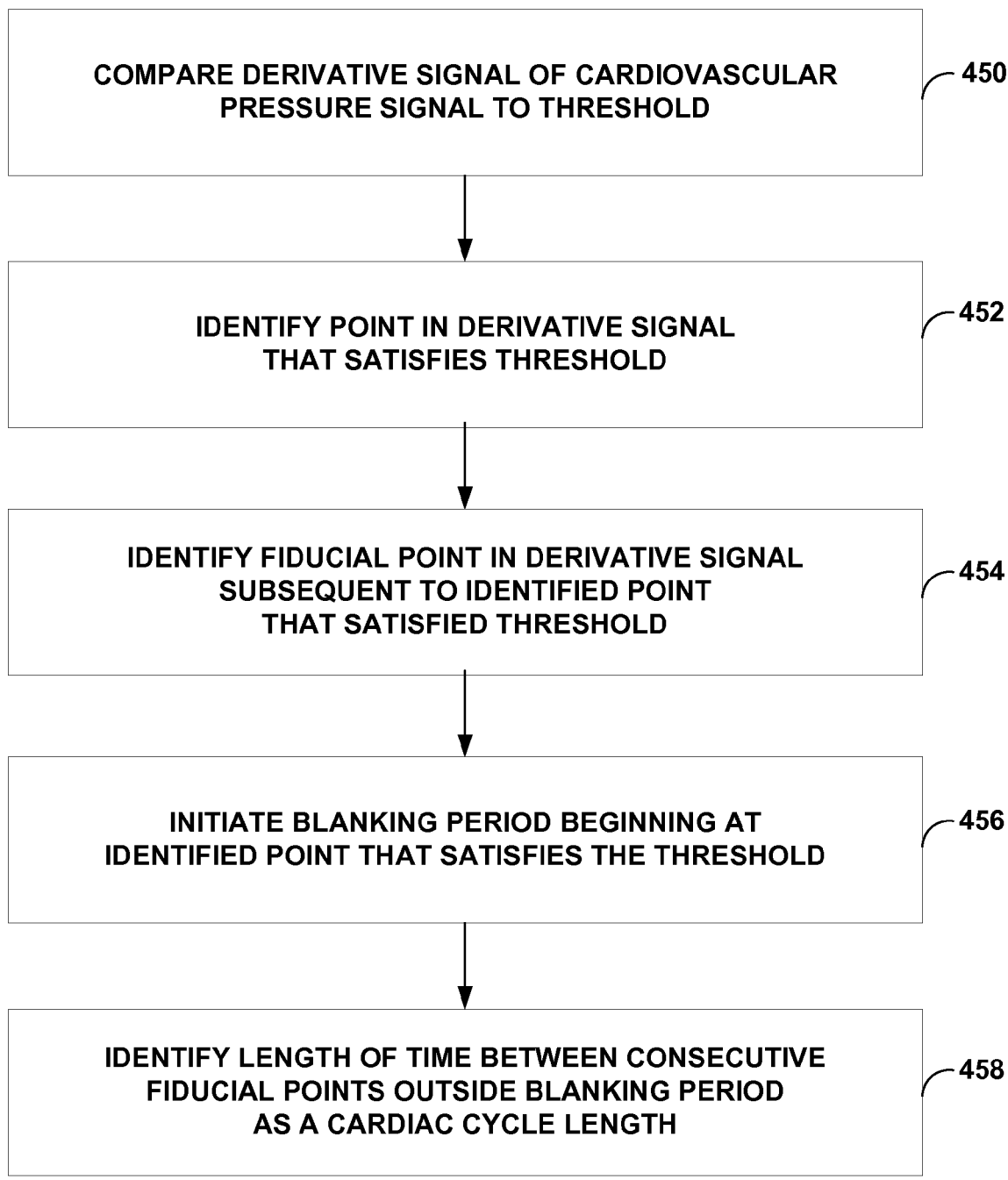
FIG. 11 is a flow diagram illustrating an exemplary method for determining a cardiac cycle length, in accordance with various techniques of this disclosure.

FIG. 11 is a flow diagram illustrating an exemplary method for determining a cardiac cycle length, in accordance with various techniques of this disclosure. A pressure analysis module, e.g., pressure analysis module 90 of IMD 16, may be used to perform some or all of the calculations described above in order to calculate a cardiac cycle length. For example, pressure sensor 92 may transmit pressure information representing pulmonary artery pressure signal 200 to processor 80 via telemetry module 88. In response, processor 80 stores the received pressure information in memory 82 as pressure data 94 and then pressure analysis module 90 processes pressure data 94 by applying a derivative filter to pressure data 94 to determine a derivative, e.g., first, second, or other higher derivative, of pulmonary artery signal 400. By applying a first order derivative filter to pulmonary artery signal 400, pressure analysis module 90 generates a derivative signal of the cardiovascular pressure signal. Pressure analysis module 90 identifies a plurality of fiducial points, i.e., time reference points, within the derivative signal of the cardiovascular pressure signal. It should be noted that, in some examples, pressure analysis module 90 processes the pressure information received from pressure sensor 92 without first storing the information in memory 82.

After identifying a plurality of fiducial points within the derivative signal of the cardiovascular pressure signal, pressure analysis module 90 identifies a length of time between consecutive ones of the fiducial points as a cardiac cycle length. For example, as indicated above, a cardiac cycle length may be measured between a first sense and a second sense, a first end-diastolic pressure and a second end-diastolic pressure, a first peak-systolic pressure and a second peak-systolic pressure, or a first maximum dP/dt and a second maximum dP/dt. In particular, pressure analysis module 90 compares the derivative signal to a threshold (450). For example, pressure analysis module 90 compares pressure signal 404 to threshold 405. Then, pressure analysis module 90 identifies a point within the derivative signal that satisfies the threshold (452). For example, pressure analysis module 90 identifies that point 406 of FIG. 10 is greater than then threshold value indicated by line 405. Pressure analysis module 90 identifies a fiducial point within the derivative signal subsequent to the identified point within the derivative signal that satisfied the threshold (454). For example, as described above, pressure analysis module 90 may identify first point of maximum value of dP/dt 410 within window 408 of FIG. 10 as a fiducial point. In another example, pressure analysis module 90 may identify first sense 406 as a fiducial point. Then, pressure analysis module 90 initiates a blanking period, e.g., blanking period 414, that begins at the first sense, e.g., point 406 (456). Finally, pressure analysis module 90 identifies a length of time between consecutive ones of the fiducial points as a cardiac cycle length (458). For example, pressure analysis module 90 identifies a length of time between points 410 and 420, or between point 406 and point 416 in FIG. 10 as a cardiac cycle length. It should be noted that the derivative signal is not compared to the threshold for identification of a subsequent one of the fiducial points during the blanking period.

Although the determination of a cardiac cycle length was described above with respect to pressure analysis module 90, as mentioned above, pressure analysis module 502 of pressure sensor 92, a pressure analysis module of programmer 24, or a pressure analysis module of another device, may be used to determine a cardiac cycle length using the techniques of this disclosure. In some examples, a pressure analysis module may be implemented in one or more devices identified herein, such as one or more processors of the devices such as pressure sensor 92, IMD 16, and programmer 24 to determine a cardiac cycle length using the techniques of this disclosure.

Figure 12:
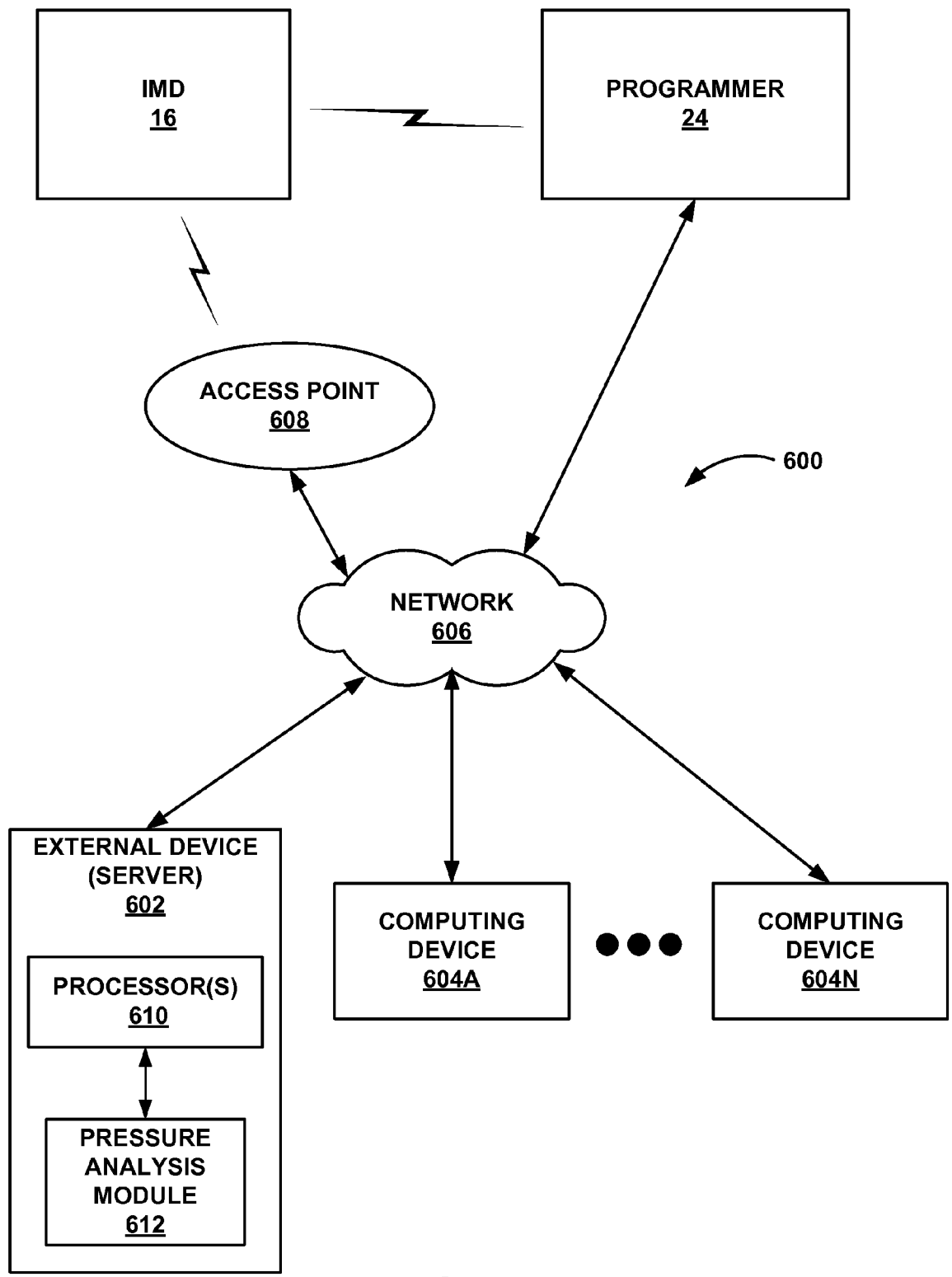
FIG. 12 is a block diagram illustrating an exemplary system that includes a server and one or more computing devices that are coupled to the IMD and the programmer shown in FIG. 1 via a network.

FIG. 12 is a block diagram illustrating an exemplary system 600 that includes an external device, such as a server 602, and one or more computing devices 604A-604N, that are coupled to the IMD 16 and programmer 24 shown in FIG. 1 via a network 606. In this example, IMD 16 may use its telemetry module 88 to communicate with programmer 24 via a first wireless connection, and to communication with an access point 608 via a second wireless connection. In the example of FIG. 12, access point 608, programmer 24, server 602, and computing devices 604A-604N are interconnected, and able to communicate with each other, through network 606. In some cases, one or more of access point 608, programmer 24, server 602, and computing devices 604A-604N may be coupled to network 606 through one or more wireless connections. IMD 16, programmer 24, server 602, and computing devices 604A-604N may each comprise one or more processors, such as one or more microprocessors, DSPs, ASICs, FPGAs, programmable logic circuitry, or the like, that may perform various functions and operations, such as those described herein.

Access point 608 may comprise a device that connects to network 606 via any of a variety of connections, such as telephone dial-up, digital subscriber line (DSL), or cable modem connections. In other examples, access point 608 may be coupled to network 606 through different forms of connections, including wired or wireless connections. In some examples, access point 608 may be co-located with patient 14 and may comprise one or more programming units and/or computing devices (e.g., one or more monitoring units) that may perform various functions and operations described herein. For example, access point 608 may include a home-monitoring unit that is co-located with patient 14 and that may monitor the activity of IMD 16.

In some cases, server 602 may be configured to provide a secure storage site for data that has been collected from IMD 16 and/or programmer 24. Network 606 may comprise a local area network, wide area network, or global network, such as the Internet. In some cases, programmer 24 or server 602 may assemble data in web pages or other documents for viewing by trained professionals, such as clinicians, via viewing terminals associated with computing devices 604A-604N. The illustrated system of FIG. 12 may be implemented, in some aspects, with general network technology and functionality similar to that provided by the Medtronic CareLink® Network developed by Medtronic, Inc., of Minneapolis, Minn.

In some examples, processor 610 of server 602 may be configured to receive pressure information from pressure sensor(s) 92 for processing by pressure analysis module 612 in the manner described throughout this disclosure. In other examples, processor 610 may received data processed by a pressure analysis module, e.g., processed data 96 processed by pressure analysis module 90 of IMD 16. Pressure analysis module 612 may determine cardiac cycle lengths, systolic pressures, and/or diastolic pressures based on the received pressure information using any of the techniques described in this disclosure. Processor 610 may provide alerts to users, e.g., to the patient via access point 608 or to a clinician via one of computing devices 604, identifying change, e.g., worsening, in patient condition based on cardiac cycle length and/or pressure metrics measured from pulmonary arterial pressures. Processor 610 may suggest to a clinician, e.g., via programmer 24 or a computing device 604, a change in a therapy, such as CRT, based on cardiac cycle length and/or pressure metrics measured from pulmonary arterial pressures. Processor 610 may also adjust or control the delivery of therapy by IMD 16, e.g., electrical stimulation therapy and/or a therapeutic substance, via network 606.

Figure 13:
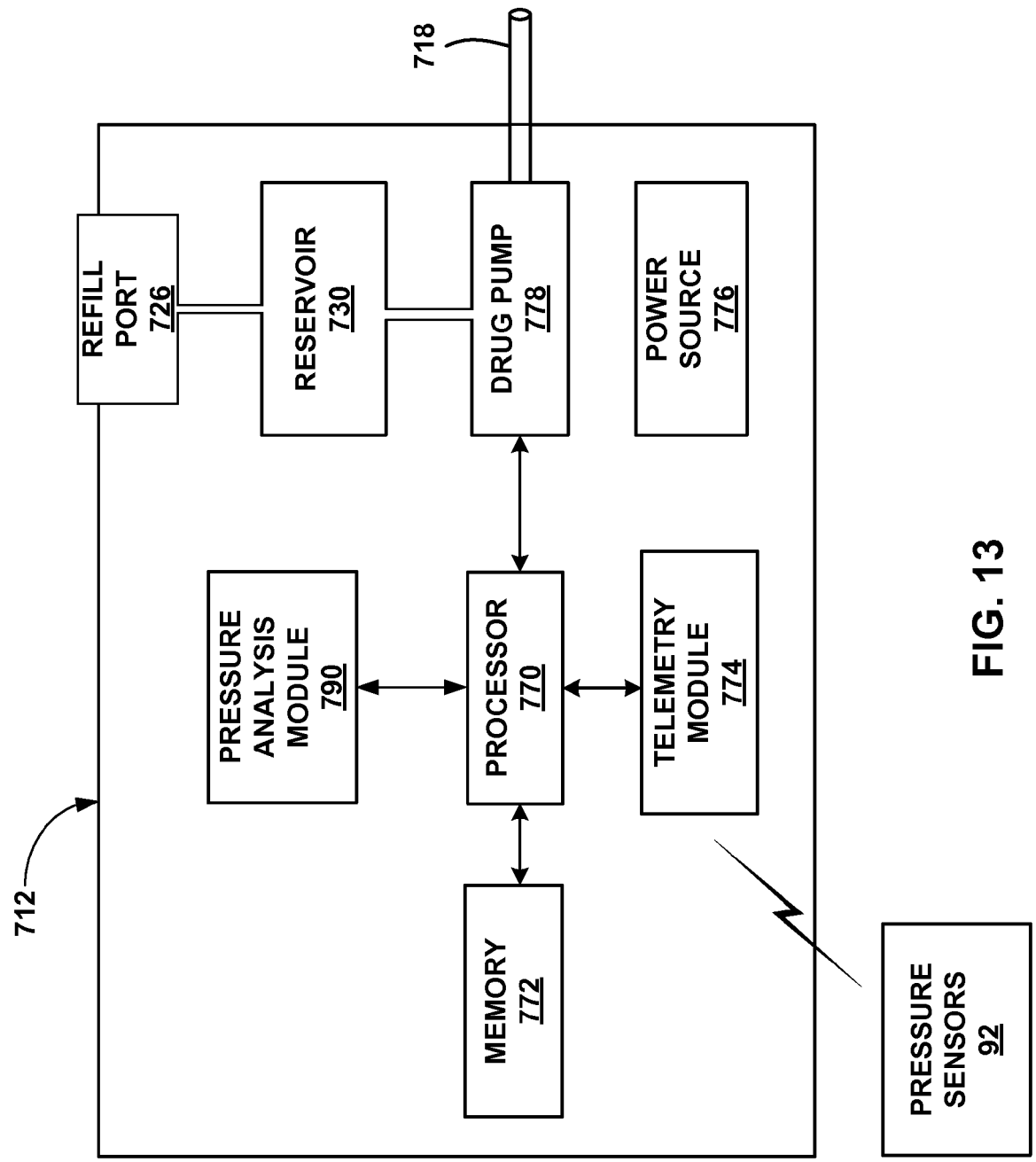
FIG. 13 is block diagram of an embodiment of another example implantable medical device.

FIG. 13 is block diagram of an embodiment of another example implantable medical device that may be used to delivery drug therapy based on the determined cycle lengths and/or various pressure metrics. IMD 712 includes fill port 726, reservoir 730, processor 770, memory 772, telemetry module 774, power source 776, and drug pump 778. Processor 770 may include a microprocessor, a controller, a digital signal processor (DSP), an application specific integrated circuit (ASIC), a field-programmable gate array (FPGA), discrete logic circuitry, or the like. Drug pump 778 may be a mechanism that delivers a therapeutic agent in some metered or other desired flow dosage to the therapy site within patient 14 from reservoir 730 via the catheter 718 based on the determined cycle lengths and/or various pressure metrics measured using the techniques of this disclosure.

Processor 770 controls the operation of drug pump 778 with the aid of instructions that are stored in memory 772. For example, the instructions may define therapy programs that specify the bolus size of a therapeutic agent that is delivered to a target tissue site within patient 14 from reservoir 730 via catheter 718. The therapy programs may also include other therapy parameters, such as the frequency of bolus delivery, the concentration of the therapeutic agent delivered in each bolus, the type of therapeutic agent delivered (if IMD 712 is configured to deliver more than one type of therapeutic agent), and so forth.

Memory 772 may include any volatile or non-volatile media, such as a random access memory (RAM), read only memory (ROM), non-volatile RAM (NVRAM), electrically erasable programmable ROM (EEPROM), flash memory, and the like. Memory 772 may store instructions for execution by processor 770, such as therapy programs and any other information regarding therapy of patient 14. Memory 772 may include separate memories for storing instructions, patient information, therapy parameters (e.g., grouped into sets referred to as "therapy programs"), and other categories of information. In some embodiments, memory 772 stores program instructions that, when executed by processor 770, cause IMD 712 and processor 770 to perform the functions attributed to them herein.

Telemetry module 774 in IMD 712, as well as telemetry modules in other devices, e.g., a patient or clinician programmer, may accomplish communication by RF communication techniques. One or more pressure sensors 92 may be in communication with IMD 712 via telemetry module 774. Pressure analysis module 790 analyzes the pressure data received from pressure sensor(s) 92. Pressure analysis module 790 may be implemented as software, firmware, hardware or any combination thereof. In some example implementations, pressure analysis module 790 may be a software process implemented in or executed by processor 770. Memory 772 is one example of a non-transitory, computer-readable storage medium that includes computer-readable instructions that, when executed by processor 770, cause IMD 712 and processor 770 to titrate deliver of a therapeutic agent based on the determined cycle lengths and/or various pressure metrics. Memory 772 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Using the various techniques described above, cardiac cycle length and/or pressure metrics such as systolic pressure and diastolic pressure may be derived from the pulmonary arterial pressure (PAP) from one or more pressure sensors in the pulmonary artery (PA) without adding electrodes to a patient.

Various example implementations of the disclosure have been described. These and other example implementations are within the scope of the following claims.

The invention claimed is:

1. A method of monitoring a cardiovascular pressure signal in a medical device, comprising:
   identifying, by the medical device, a point within a derivative signal of the cardiovascular pressure signal without reference to electrical activity of a heart;
   initiating, by the medical device, a time window that begins at the identified point in the derivative signal, wherein the time window comprises one of a fixed temporal length or a variable temporal length, and wherein the variable temporal length is determined based on a plurality of cardiac cycle lengths;
   identifying, with the medical device, a point within the cardiovascular pressure signal within the time window; and
   determining, with the medical device, at least one of a systolic pressure or a diastolic pressure based on the identified point within the cardiovascular pressure signal.

2. The method of claim 1, wherein the derivative signal is a first derivative signal, wherein identifying, by the medical device, the point within the first derivative signal of the cardiovascular pressure signal without reference to electrical activity of the heart comprises identifying a maximum value of the first derivative signal as the point within the first derivative signal.

3. The method of claim 2,
   wherein the time window begins at and extends forward in time from the identified maximum value of the first derivative signal,
   wherein identifying, with the medical device, the point within the cardiovascular pressure signal within the time window comprises identifying a point of maximum value within the cardiovascular pressure signal within the time window, and
   wherein determining, with the medical device, at least one of the systolic pressure or the diastolic pressure based on the identified point comprises determining the systolic pressure based on the identified point of maximum value within the cardiovascular pressure signal within the time window.

4. The method of claim 2, wherein the time window begins at and extends backward in time from the identified maximum value of the first derivative signal, the method further comprising:
   identifying, with the medical device, a point within a second derivative signal of the cardiovascular pressure signal within the time window without reference to electrical activity of the heart.

5. The method of claim 4,
   wherein the point within the second derivative signal of the cardiovascular pressure signal is a point of maximum second derivative within the time window,
   wherein identifying, with the medical device, the point within the cardiovascular pressure signal within the time window comprises identifying the point within the cardiovascular pressure signal within the time window that corresponds in time to the identified point of maximum second derivative, and
   wherein determining, with the medical device, at least one of the systolic pressure or the diastolic pressure based on the identified point comprises determining the diastolic pressure based on the identified point within the cardiovascular pressure signal within the time window that corresponds in time to the identified point of maximum second derivative.

6. The method of claim 1, wherein the time window comprises the variable temporal length.

7. The method of claim 1, wherein the time window comprises the fixed temporal length.

8. The method of claim 1, further comprising:
   controlling delivery of at least one of electrical stimulation and a therapeutic agent based on the determination.

9. A medical device system for monitoring a cardiovascular pressure signal, comprising:
   at least one pressure sensor to generate the cardiovascular pressure signal; and
   at least one pressure analysis module configured to:
   identify a point within a derivative signal of the cardiovascular pressure signal without reference to electrical activity of a heart;
   initiate a time window that begins at the identified point in the derivative signal, wherein the time window comprises one of a fixed temporal length or a variable temporal length, and wherein the variable temporal length is determined based on a plurality of cardiac cycle lengths;
   identify a point within the cardiovascular pressure signal within the time window; and determine at least one of a systolic pressure or a diastolic pressure based on the identified point within the cardiovascular pressure signal.

10. The system of claim 9, wherein the derivative signal is a first derivative signal, wherein the at least one pressure analysis module configured to identify the point within the first derivative signal of the cardiovascular pressure signal without reference to electrical activity of the heart is configured to identify a maximum value of the first derivative signal as the point within the first derivative signal.

11. The system of claim 10,
wherein the time window begins at and extends forward in time from the identified maximum value of the first derivative signal,
wherein the at least one pressure analysis module configured to identify the point within the cardiovascular pressure signal within the time window is configured to identify a point of maximum value within the cardiovascular pressure signal within the time window, and
wherein at least one pressure analysis module configured to determine at least one of the systolic pressure or the diastolic pressure based on the identified point is configured to determine the systolic pressure based on the identified point of maximum value within the cardiovascular pressure signal within the time window.

12. The system of claim 10, wherein the time window begins at and extends backward in time from the identified maximum value of the first derivative signal, and the at least one pressure analysis module is further configured to:
identify a point within a second derivative signal of the cardiovascular pressure signal within the time window without reference to electrical activity of the heart.

13. The system of claim 12,
wherein the point within the second derivative signal of the cardiovascular pressure signal is a point of maximum second derivative within the time window,
wherein the at least one pressure analysis module configured to identify the point within the cardiovascular pressure signal within the time window is configured to identify the point within the cardiovascular pressure signal within the time window that corresponds in time to the identified point of maximum second derivative, and
wherein the at least one pressure analysis module configured to determine at least one of the systolic pressure or the diastolic pressure based on the identified point is configured to determine the diastolic pressure based on the identified point within the cardiovascular pressure signal within the time window that corresponds in time to the identified point of maximum second derivative.

14. The system of claim 9, wherein the time window comprises the variable temporal length.

15. The system of claim 9, wherein the time window has a length that is fixed.

16. The system of claim 9, further comprising:
at least one medical device configured to deliver at least one of electrical stimulation and a therapeutic agent based on the determination.

17. A computer-readable storage medium comprising instructions that, when executed, cause a cardiovascular pressure analysis module of a medical device to:
identify a point within a derivative signal of a cardiovascular pressure signal without reference to electrical activity of a heart;
initiate a time window that begins at the identified point in the derivative signal; identify a point within the cardiovascular pressure signal within the time window, wherein the time window comprises one of a fixed temporal length or a variable temporal length, and wherein the variable temporal length is determined based on a plurality of cardiac cycle lengths; and
determine at least one of a systolic pressure or a diastolic pressure based on the identified point within the cardiovascular pressure signal.

18. The computer-readable storage medium of claim 17, wherein the derivative signal is a first derivative signal, and
wherein the instructions that, when executed, cause the pressure analysis module to identify the point within the derivative signal of the cardiovascular pressure signal without reference to electrical activity of the heart comprise instructions that, when executed, cause the cardiovascular pressure analysis module to identify a maximum value of the first derivative signal, as the point within the first derivative signal.

19. The computer-readable storage medium of claim 18,
wherein the time window begins at and extends forward in time from the identified maximum value of the first derivative signal,
wherein the instructions that, when executed, cause the pressure analysis module to identify the point within the cardiovascular pressure signal within the time window comprise instructions that, when executed, cause the cardiovascular pressure analysis module to identify a point of maximum value within the cardiovascular pressure signal within the time window, and
wherein the instructions that, when executed, cause the cardiovascular pressure analysis module to determine at least one of the systolic pressure or the diastolic pressure based on the identified point comprise instructions that, when executed, cause the cardiovascular pressure analysis module to determine the systolic pressure based on the identified point of maximum value within the cardiovascular pressure signal within the time window.

20. The computer-readable storage medium of claim 18,
wherein the time window begins at and extends backward in time from the identified maximum value of the first derivative signal, the computer-readable storage medium further comprising instructions that, when executed, cause the cardiovascular pressure analysis module to:
identify a point within a second derivative signal of the cardiovascular pressure signal within the time window without reference to electrical activity of the heart.

21. The computer-readable storage medium of claim 20,
wherein the point within the second derivative signal of the cardiovascular pressure signal is a point of maximum second derivative within the time window,
wherein the instructions that, when executed, cause the cardiovascular pressure analysis module to identify the point within the cardiovascular pressure signal within the time window comprise instructions that, when executed, cause the cardiovascular pressure analysis module to identify the point within the cardiovascular pressure signal within the time window that corresponds in time to the identified point of maximum second derivative, and
wherein the instructions that, when executed, cause the cardiovascular pressure analysis module to determine at least one of the systolic pressure or the diastolic pressure based on the identified point comprise instructions that, when executed, cause the cardiovascular pressure analysis module to determine the diastolic pressure based on the identified point within the cardiovascular pressure signal within the time window that corresponds in time to the identified point of maximum second derivative.

22. The computer-readable storage medium of claim 17, wherein the time window comprises the variable temporal length.

23. The computer-readable storage medium of claim 17, wherein the time window comprises the fixed temporal length.

24. The computer-readable storage medium of claim 17, further comprising instructions that, when executed, cause the cardiovascular pressure analysis module of the medical device to:
 control, based on the determination, delivery of at least one of electrical stimulation and a therapeutic agent.

25. The method of claim 1, wherein the fixed temporal length and the variable temporal length are less than a cardiac cycle length of a cardiac cycle for at least one of the systolic pressure or the diastolic pressure.

* * * * *